United States Patent
Liu et al.

(10) Patent No.: US 12,351,550 B2
(45) Date of Patent: Jul. 8, 2025

(54) SEPARATION PROCESSES FOR PYROLYSIS PRODUCTS OF ANNULAR JET VORTEX CHAMBER REACTOR

(71) Applicant: SABIC GLOBAL TECHNOLOGIES B.V., Bergen op Zoom (NL)

(72) Inventors: Zheng Liu, Bangalore (IN); Murali Gopalakrishnan, Bangalore (IN); Stephen Keith Turner, Bangalore (IN); Sreekanth Pannala, Bangalore (IN)

(73) Assignee: SABIC Global Technologies B.V., Bergen op Zoom (NL)

( * ) Notice: Subject to any disclaimer, the term of this patent is extended or adjusted under 35 U.S.C. 154(b) by 115 days.

(21) Appl. No.: 18/548,821

(22) PCT Filed: Mar. 7, 2022

(86) PCT No.: PCT/EP2022/055723
§ 371 (c)(1),
(2) Date: Sep. 1, 2023

(87) PCT Pub. No.: WO2022/189343
PCT Pub. Date: Sep. 15, 2022

(65) Prior Publication Data
US 2024/0150260 A1 May 9, 2024

(30) Foreign Application Priority Data
Mar. 12, 2021 (EP) .................... 21162308

(51) Int. Cl.
*C07C 4/02* (2006.01)
(52) U.S. Cl.
CPC .................... *C07C 4/025* (2013.01)
(58) Field of Classification Search
CPC ........... C07C 4/02; C07C 4/025; C10G 9/002; C10G 9/38; C10K 1/005
See application file for complete search history.

(56) References Cited

U.S. PATENT DOCUMENTS

| 2,823,243 A | 2/1958 | Robinson |
| 2,836,635 A | 5/1958 | Herbert et al. |

(Continued)

FOREIGN PATENT DOCUMENTS

| CN | 102294242 B | 4/2014 |
| EP | 1063273 A1 | 12/2000 |

(Continued)

OTHER PUBLICATIONS

Panala (Year: 2020).*

(Continued)

*Primary Examiner* — Sharon Pregler
(74) *Attorney, Agent, or Firm* — Fish & Richardson P.C.

(57) ABSTRACT

A process for producing ethylene comprising introducing fuel, ethane/higher hydrocarbons, oxygen, steam to annular jet vortex chamber having combustion upstream of cracking to provide swirling fluid flow pattern producing cracking product (ethylene, acetylene, ethane, methane, 10-60 wt. % water, $CO_2$, CO, hydrogen, oxygenates) having first temperature; cooling cracking product with residence <2,000 milliseconds yielding first cooled product having second temperature lowered by ≥30° C.; cooling first cooled product yielding second cooled product having third temperature lowered by ≥300° C. and heated heat exchange medium; separating second cooled product into removed water (water, oxygenates), and cracked gas (ethylene, acetylene, ethane, methane, $CO_2$, CO, hydrogen) introduced to continuous regeneration $CO_2$ removal unit producing $CO_2$-lean gas having at least 10× less $CO_2$; introducing $CO_2$-lean gas to once-through $CO_2$ removal unit producing $CO_2$-depleted gas (ethylene, acetylene, ethane, methane, CO, hydrogen); separating $CO_2$-depleted gas into ethylene, ethane, tail gas (methane, CO, hydrogen).

16 Claims, 4 Drawing Sheets

(56) References Cited

U.S. PATENT DOCUMENTS

| | | |
|---|---|---|
| 2,941,021 A | 6/1960 | Walter et al. |
| 4,134,824 A | 1/1979 | Kamm et al. |
| 5,220,097 A | 6/1993 | Lam et al. |
| 2010/0234476 A1 | 9/2010 | Lin et al. |
| 2014/0058149 A1 | 2/2014 | Negiz et al. |

FOREIGN PATENT DOCUMENTS

| | | | |
|---|---|---|---|
| GB | 840664 A | 7/1960 | |
| WO | 2019173570 A1 | 9/2019 | |
| WO | WO-2020086681 A2 * | 4/2020 | ............ B01J 12/005 |

OTHER PUBLICATIONS

Foreign communication from related application—International Search Report and Written Opinion dated May 25, 2022 for application No. PCT/EP2022/055723 filed Mar. 7, 2022, 9 pages.

Foreign communication from related application—International Preliminary Report on Patentability dated Sep. 12, 2023 for application No. PCT/EP2022/055723 filed Mar. 7, 2022, 7 pages.

\* cited by examiner

SEPARATION PROCESSES FOR PYROLYSIS PRODUCTS OF ANNULAR JET VORTEX CHAMBER REACTOR

CROSS-REFERENCE TO RELATED APPLICATIONS

This application is a National Stage Application under 35 U.S.C. § 371 and claims the benefit of International Application No. PCT/EP2022/055723, filed Mar. 7, 2022, which claims priority to EP 21162308.7, filed Mar. 12, 2021, the contents of which are incorporated herein in its entirety.

TECHNICAL FIELD

The present disclosure relates to methods of producing hydrocarbons, more specifically methods of producing olefins with an annular jet vortex chamber reactor.

BACKGROUND

Hydrocarbons, and specifically olefins such as ethylene, can be typically used to produce a wide range of products, for example, break-resistant containers and packaging materials. Currently, for industrial scale applications, ethylene is produced by heating natural gas condensates and petroleum distillates, which include ethane and higher hydrocarbons, and the produced ethylene is separated from a product mixture by using gas separation processes.

Conventional steam cracking processes display several disadvantages, such as heat losses; complexity associated with separate exothermic (combustion in the furnace) and endothermic (cracking in process tubes) steps; plugging from coking; lack of feedstock flexibility; etc. Conventional ethane steam crackers generally yield a steam cracker effluent with a specific composition (e.g., specific amounts of ethylene, water, carbon dioxide, etc.) that is processed with a conventional steam cracker separation train configuration. Cracking reactors other than conventional ethane steam crackers may yield reactor effluents with compositions that are different (e.g., different amounts of water, carbon monoxide, carbon dioxide, acetylene, etc.), where such different reactor effluents may not be processed with conventional steam cracker separation trains owing to different effluent volume, composition, and/or physical properties. Thus, there is an ongoing need for the development of ethylene production processes.

BRIEF DESCRIPTION OF THE DRAWINGS

For a detailed description of the preferred aspects of the disclosed methods, reference will now be made to the accompanying drawings in which.

DETAILED DESCRIPTION

Figure 1:
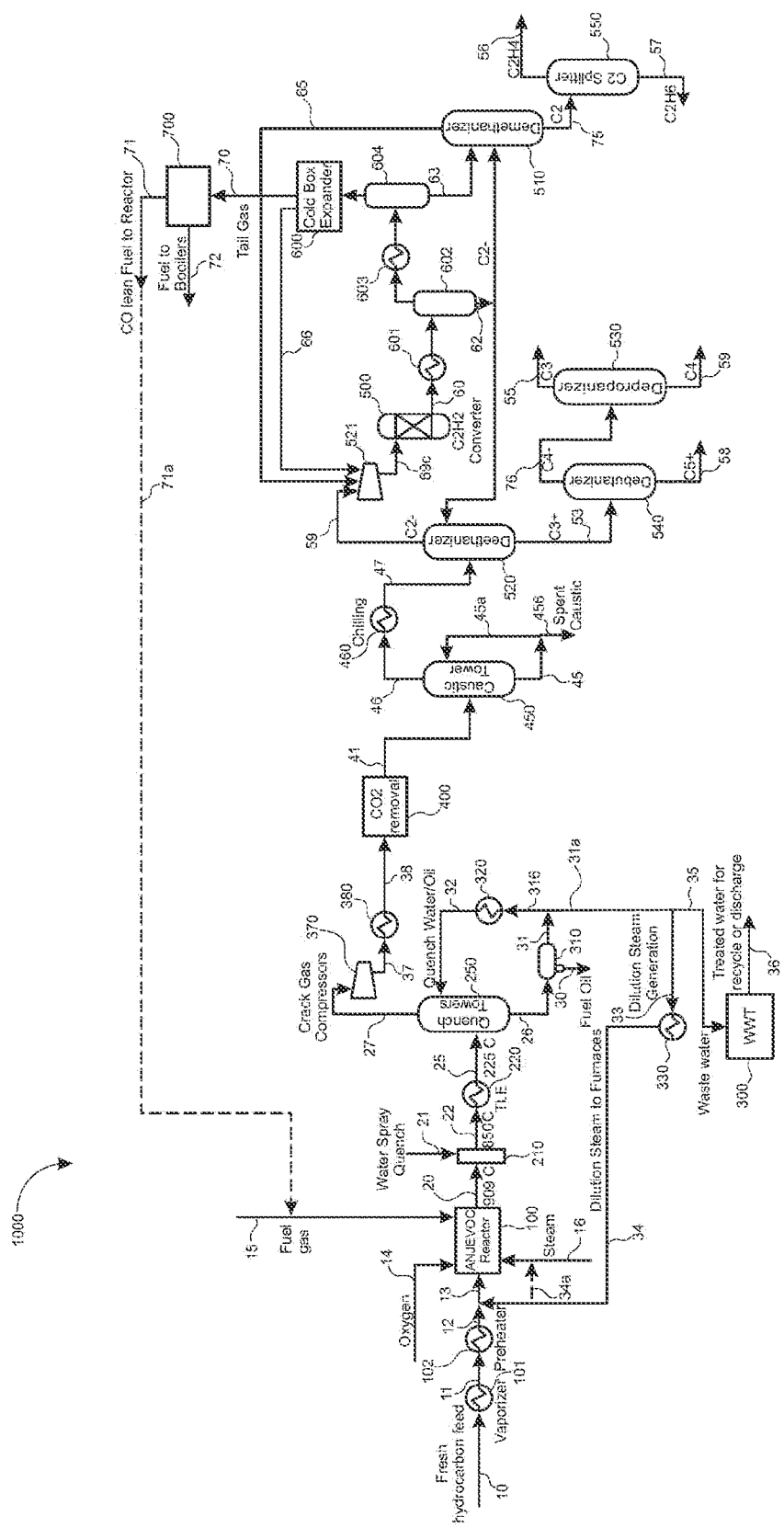
FIG. 1 displays a configuration of an ethylene production system.

Disclosed herein are processes for producing olefins, such as ethylene. Disclosed herein are processes for producing ethylene with an annular jet vortex chamber (ANJEVOC) reactor, wherein specific separation processes have to be employed to recover the ethylene from the pyrolysis products of the ANJEVOC. The ANJEVOC will be discussed in more detail later herein. Even with a substantially similar feed of hydrocarbons, the effluent of the ANJEVOC is different in composition and conditions from effluents of conventional hydrocarbon cracking units, such as ethane steam crackers. The process for producing ethylene as disclosed herein comprises specific separation steps that are required for processing the unique efflux of the ANJEVOC in order to obtain final olefin products (e.g., ethylene) of specific purities; while recycling and/or utilizing other valuable components recovered from the separation steps as feed and/or fuel.

Other than in the operating examples or where otherwise indicated, all numbers or expressions referring to quantities of ingredients, reaction conditions, and the like, used in the specification and claims are to be understood as modified in all instances by the term "about." Various numerical ranges are disclosed herein. Because these ranges are continuous, they include every value between the minimum and maximum values. The endpoints of all ranges reciting the same characteristic or component are independently combinable and inclusive of the recited endpoint. Unless expressly indicated otherwise, the various numerical ranges specified in this application are approximations. The endpoints of all ranges directed to the same component or property are inclusive of the endpoint and independently combinable. The term "from more than 0 to an amount" means that the named component is present in some amount more than 0, and up to and including the higher named amount.

The terms "a," "an," and "the" do not denote a limitation of quantity, but rather denote the presence of at least one of the referenced item. As used herein the singular forms "a," "an," and "the" include plural referents.

As used herein, "combinations thereof" is inclusive of one or more of the recited elements, optionally together with a like element not recited, e.g., inclusive of a combination of one or more of the named components, optionally with one or more other components not specifically named that have essentially the same function. As used herein, the term "combination" is inclusive of blends, mixtures, alloys, reaction products, and the like.

Reference throughout the specification to "an aspect," "another aspect," "other aspects," "some aspects," and so forth, means that a particular element (e.g., feature, structure, property, and/or characteristic) described in connection with the aspect is included in at least an aspect described herein, and may or may not be present in other aspects. In addition, it is to be understood that the described element(s) can be combined in any suitable manner in the various aspects.

As used herein, the terms "inhibiting" or "reducing" or "preventing" or "avoiding" or any variation of these terms, include any measurable decrease or complete inhibition to achieve a desired result.

As used herein, the term "effective," means adequate to accomplish a desired, expected, or intended result.

As used herein, the terms "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains") are inclusive or open-ended and do not exclude additional, unrecited elements or method steps.

Unless defined otherwise, technical and scientific terms used herein have the same meaning as is commonly understood by one of skill in the art.

Compounds are described herein using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through the carbon of the carbonyl group.

As used herein, the terms "$C_x$ hydrocarbons" and "$C_x$s" are interchangeable and refer to any hydrocarbon having x number of carbon atoms (C). For example, the terms "$C_4$ hydrocarbons" and "$C_4$s" both refer to any hydrocarbons having exactly 4 carbon atoms, such as n-butane, iso-butane, cyclobutane, 1-butene, 2-butene, isobutylene, butadiene, and the like, or combinations thereof.

As used herein, the term "$C_{x+}$ hydrocarbons" refers to any hydrocarbon having equal to or greater than x carbon atoms (C). For example, the term "$C_{2+}$ hydrocarbons" refers to any hydrocarbons having 2 or more carbon atoms, such as ethane, ethylene, $C_3$s, $C_4$s, $C_5$s, etc.

As used herein, the term "$C_{x-}$ hydrocarbons" refers to any hydrocarbon having equal to or less than x carbon atoms (C). For example, the term "$C_{2-}$ hydrocarbons" refers to any hydrocarbons having 2 or less carbon atoms, such as ethane, ethylene, acetylene, and methane.

Referring to FIG. 1, an ethylene production system 1000 is disclosed. The ethylene production system 1000 generally comprises an annular jet vortex chamber (ANJEVOC) 100; a first cracking product cooling zone 210; a cracking product heat exchanger 220; a quench tower 250; a waste water treatment (WWT) unit 300; a continuous regeneration carbon dioxide ($CO_2$) removal unit 400; a once-through $CO_2$ removal unit 450; an acetylene converter 500; a demethanizer 510; a deethanizer 520; a depropanizer 530; a debutanizer 540; a $C_2$ splitter 550; a carbon monoxide (CO) rejection unit 700; compressors 370, 521; heat exchangers 101, 102, 320, 330, 380, 460, 601, 603; separators 310, 602, 604; and a cold box unit 600.

Figure 2:
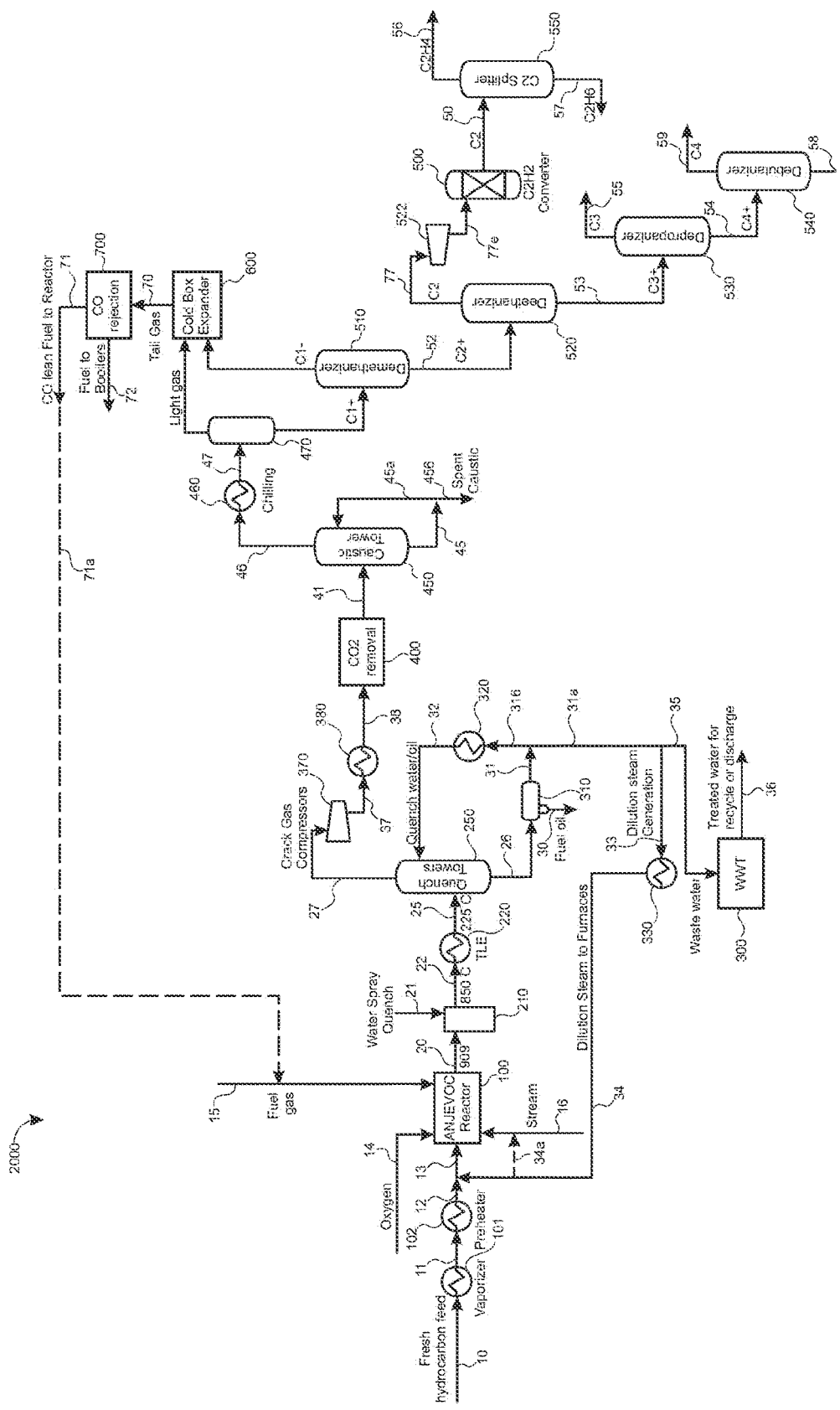
FIG. 2 displays another configuration of an ethylene production system.

Referring to FIG. 2, an ethylene production system 2000 is disclosed. The ethylene production system 2000 generally comprises an ANJEVOC 100; a first cracking product cooling zone 210; a cracking product heat exchanger 220; a quench tower 250; a WWT unit 300; a continuous regeneration $CO_2$ removal unit 400; a once-through $CO_2$ removal unit 450; an acetylene converter 500; a demethanizer 510; a deethanizer 520; a depropanizer 530; a debutanizer 540; a $C_2$ splitter 550; a CO rejection unit 700; a compressor(s) 370; an expander 522; heat exchangers 101, 102, 320, 330, 380, 460; and separators 310, 470; and a cold box unit 600. As will be appreciated by one of skill in the art, and with the help of this disclosure, ethylene production system components shown in FIGS. 1 and 2 can be in fluid communication with each other (as represented by the connecting lines indicating a direction of fluid flow) through any suitable conduits (e.g., pipes, streams, etc.). Common reference numerals refer to common components present in one or more of the Figures, and the description of a particular component is generally applicable across respective Figures wherein the component is present, except as otherwise indicated herein. While the current disclosure will be discussed in detail in the context of ethylene production systems having the configurations of FIGS. 1 and 2, it should be understood that any suitable type of ethylene production systems can be used for carrying out the process for producing ethylene as disclosed herein; for example an ethylene production system having different system components and/or different connecting streams between system components when compared to the configurations of FIGS. 1 and 2. Further, it should be noted that while the ethylene production systems having the configurations of FIGS. 1 and 2 displays single units or sections for the various process steps, each unit or section could be composed of one or more units that may operate in conjunction with one another, such as parallel or sequentially, to carry out the various described process steps.

In an aspect, a process for producing ethylene as disclosed herein can comprise a step of introducing a fuel gas 15, hydrocarbons (e.g., a fresh hydrocarbon feed stream, such as stream 10), an oxidant gas 14, and steam 16 to an ANJEVOC 100 to provide for a swirling fluid flow pattern within the ANJEVOC 100; wherein the ANJEVOC 100 comprises a combustion zone and a cracking zone; wherein the combustion zone is upstream of the cracking zone; wherein the oxidant gas 14 does not contact the fuel gas 15 outside of the ANJEVOC 100; wherein the oxidant gas 14 does not contact the hydrocarbons 10 outside of the ANJEVOC 100; wherein the hydrocarbons 10 comprise ethane and/or saturated hydrocarbons other than ethane; wherein at least a portion of the fuel gas 15 and at least a portion of the oxidant gas 14 contact each other in the combustion zone to produce a combustion product; wherein the combustion product comprises water and carbon dioxide; wherein the swirling fluid flow pattern provides for conveying at least a portion of the combustion product to the cracking zone; wherein the combustion product heats the hydrocarbons 10 in the cracking zone to a temperature effective for a cracking reaction; and wherein at least a portion of the hydrocarbons 10 undergoes a cracking reaction in the cracking zone to produce a cracking product 20. By employing highly swirling flows, the design of the ANJEVOC 100 displays several advantages over conventional hydrocarbon cracking units. For example, the ANJEVOC 100 can advantageously provide for efficient heat transfer while minimizing mass transfer; the ANJEVOC 100 can advantageously dial in temperatures and residence times for increased efficiency with respect to olefin yields; the ANJEVOC 100 can advantageously reduce plugging from coking; etc. Generally, conventional commercial crackers are typically optimized for only certain types of feedstocks, while ANJEVOC 100 can handle much broader ranges of feedstocks, advantageously varying from naphtha, propane, butane, and ethane to even methane for producing olefin products such as ethylene. For purposes of the disclosure herein, the terms "upstream" and "downstream" are used to refer to the position of a system component with respect to the overall fluid flow through the system component.

Feed streams may be introduced to the ANJEVOC 100 via feed inlets, such as annular feed inlets. The oxidant gas 14 is introduced to the ANJEVOC 100 via a feed inlet separate from the feed inlets for the fuel gas 15 and hydrocarbons 10, to minimize the risk of explosion. The oxidant gas 14 may be combined with steam prior to introducing to the ANJEVOC 100. The fuel gas 15 and/or hydrocarbons 10 may also be combined with steam prior to introducing to the ANJEVOC 100. For example, hydrocarbons (e.g., cracking feed, hydrocarbon feed to be cracked, such as hydrocarbons 10, 11, 12) may be contacted with steam 34 to produce stream 13, wherein stream 13 introduces both hydrocarbons and steam to the ANJEVOC 100. The feed streams may enter the ANJEVOC 100 via annular feed inlets that provide for the entering gasses flowing in an inwardly swirling fluid flow pattern about a central axis of the ANJEVOC 100, with the fuel gas combusting in the combustion zone to form a combustion product (e.g., heated combustion gases). The combustion product generally comprises combustion products, such as $CO_2$ and water ($H_2O$), as well as carbon monoxide (CO), minor oxygenated species and other species, and some unconverted hydrocarbons (e.g., hydrocarbons that were present in the fuel gas and did not combust). In some aspects, the feed streams may enter the ANJEVOC 100 substantially perpendicularly to the central axis of the ANJEVOC 100 in an inwardly swirling fluid flow pattern that flows about the central axis of the ANJEVOC 100, with the fuel gas combusting in the combustion zone to form heated combustion gases. The ANJEVOC 100 may further comprise a mixing zone, wherein the mixing zone is upstream of the cracking zone (e.g., reaction zone) and downstream of the combustion zone. In some aspects, the mixing zone may be the initial or upstream portion of the cracking zone, such as the portion of the cracking zone first encountered by the gases flowing through the ANJEVOC 100 from the combustion zone and/or feed inlets to the cracking zone.

The combustion product (e.g., heated combustion gases), cracking feed (e.g., hydrocarbons to be cracked, such as hydrocarbons from stream 10), and steam can pass into the mixing zone or upstream portion of the cracking zone, such that the heated combustion gases, cracking feed, and steam are mixed together and form a swirling, heated gas mixture within the mixing zone or upstream portion of the cracking zone. The swirling, heated gas mixture travels downstream through the cracking zone under reaction conditions suitable for hydrocarbon cracking, wherein at least a portion of the hydrocarbons of the cracking feed is converted to cracked hydrocarbon products. A cracking product (e.g., cracked hydrocarbon product) 20 can exit the ANJEVOC 100 (e.g., the cracking zone or reaction zone of the ANJEVOC 100), for example via an effluent outlet (e.g., ANJEVOC outlet).

In an aspect, the fuel gas 15 may comprise hydrogen ($H_2$) and/or methane ($CH_4$). The fuel gas 15 may be fed to the ANJEVOC 100 as a separate stream and/or mixed with steam. In some aspects where both $H_2$ and $CH_4$ are used in the fuel gas 15, the $CH_4$ may be present in the fuel gas 15 in an amount of less than about 20 mol %, alternatively less than about 15 mol %, alternatively less than about 10 mol %, or alternatively less than about 5 mol %. In other aspects, however, greater amounts of $CH_4$ may be used in the fuel gas 15, including 100% $CH_4$. In yet other aspects, natural gas may also be used as the fuel gas 15. In still yet other aspects, the fuel gas 15 may be a hydrogen-rich gas stream, such as a recycled stream (e.g., CO-lean gas 71) and/or additional hydrogen gas. The hydrogen-rich gas stream may contain other components such as $CH_4$, CO, steam, and $CO_2$. In still yet other aspects, hydrocarbons other than $CH_4$ and/or natural gas can also be used as the fuel gas 15. $N_2$ and/or sulfur can also be present. When sulfur is present in the fuel gas 15 and/or any other feed streams to the ANJEVOC 100, additional separation may be necessary downstream.

In an aspect, the oxidant gas 14 may be a concentrated oxygen-gas feed, wherein a majority of the feed (i.e., greater than about 50 mol %) comprises oxygen gas (02). The oxidant gas 14 may be fed to the ANJEVOC 100 as a separate stream and/or mixed with steam. The oxidant gas 14 may be a high-purity oxygen-containing gas feed comprising $O_2$ in an amount of from about 20 mol % to about 100 mol %. A high-purity oxygen-containing gas feed may be provided by an air separation unit that may be used for separating oxygen gas from air or other oxygen-gas source. In some aspects, air may also be used as the oxidant gas 14. However, where air is used as the oxidant gas 14, or in cases where there are large amounts of impurities (e.g., S, Cl, $N_2$) in the oxidant gas 14, separation of such impurities from the cracking product may be necessary downstream.

Steam or water may be introduced to the ANJEVOC 100, as a separate stream (34a, 16) and/or mixed in with other feed streams (34, 13). In aspects where sufficient steam is provided to the ANJEVOC 100 mixed in with the other feed streams, the separate steam stream (34a, 16) may be eliminated. In some aspects, steam may be introduced to the ANJEVOC 100 in a mass ratio of steam to fuel gas of from greater than 0 to about 2.

The cracking feed (e.g., hydrocarbons, a fresh hydrocarbon feed stream, such as stream 10) can include saturated hydrocarbons such as ethane, as well as liquefied petroleum gas (LPG), butane, naphtha, natural gas, light gas oils, heavy gas oils, and/or plastic or bio-based hydrocarbon feeds. In an aspect, the cracking feed may comprise ethane and/or saturated hydrocarbons other than ethane, such as butane. The cracking feed (e.g., hydrocarbons, a fresh hydrocarbon feed stream, such as stream 10) can be pre-heated in pre-heaters (e.g., electrical heaters, heat exchangers, etc.) by indirect heat exchange before being heated to a reaction temperature (e.g., temperature effective for a pyrolysis reaction) by direct heat exchange through contact with the combustion product. As will be appreciated by one of skill in the art, and with the help of this disclosure, the terms "direct heat exchange" and "indirect heat exchange" are known to one of skill in the art.

In an aspect, stream 10 may be preheated prior to being introduced into the ANJEVOC 100. For example, stream 10 may be preheated in vaporizer 101 to yield a heated stream 11 and/or in preheater 102 to yield heated stream 12. In some aspects, at least a portion of the hydrocarbon streams 10, 11, 12 may be introduced to the ANJEVOC 100. In other aspects, at least a portion of the hydrocarbon streams 10, 11, 12 may be mixed with steam 34 to form a steam-hydrocarbon stream 13, wherein at least a portion of the steam-hydrocarbon stream 13 may be introduced to the ANJEVOC 100. The hydrocarbon stream (e.g., fresh hydrocarbon stream 10) may be heated to a temperature of from about 25° C. to about 500° C. to improve conversion efficiency and/or vaporize heavier liquid hydrocarbons (wherein heavier liquid hydrocarbons may be vaporized either externally or within the reactor). In some aspects, impurities and contaminants can be removed from the fuel gas 15 and/or hydrocarbons 10 prior to introducing to the ANJEVOC.

As will be appreciated by one of skill in the art, and with the help of this disclosure, based upon the composition of cracking feed (e.g., hydrocarbons stream 10), the operational conditions of the ANJEVOC 100 may vary. The oxidant gas 14 can be typically used with excess fuel gas such that substantially all the oxygen is consumed. In some aspects, the amount of fuel gas (e.g., hydrogen) may be from about 1 to about 4 times, or alternatively from about 2 to about 4 times the stoichiometric amount needed for combustion with oxygen. The oxidant gas 14 may provide an oxygen equivalent-to-fuel mole ratio of from about 0.125 to about 0.50, or alternatively from about 0.25 to about 0.50. Furthermore, the mass ratio between the cracking feed (e.g., hydrocarbons stream 10) and fuel gas (e.g., hydrogen) may typically range from about 1:1 to about 15:1, or alternatively from about 1:1 to about 10:1.

Without wishing to be limited by theory, the gas feed streams (e.g., fuel gas 15, hydrocarbons stream 10, oxidant gas 14, steam 16) may be introduced to the ANJEVOC 100 to provide different flow velocities to provide for Kelvin-Helmholtz instability for enhanced mixing. The flow velocities of the gas feed streams (e.g., fuel gas 15, hydrocarbons stream 10, oxidant gas 14, steam 16) may range from about 10 m/s to about 500 m/s, or alternatively from about 100 m/s to about 400 m/s. The pressure at the ANJEVOC outlet may vary. For example, an ANJEVOC outlet pressure may be from about 0 kPag to about 10,000 kPag, alternatively from about 0 kPag to about 2,000 kPag, alternatively from about 0 kPag to about 1,000 kPag, alternatively from about 100 kPag to about 2,000 kPag, or alternatively from about 100 kPag to about 1,000 kPag. In some aspects, the ANJEVOC 100 may be operated at a pressure of from about 100 kPag to about 2,000 kPag, with a gas residence time within the ANJEVOC 100 of less than about 500 milliseconds, alternatively less than about 250 milliseconds, alternatively less than about 100 milliseconds, alternatively less than about 50 milliseconds, alternatively less than about 20 milliseconds, or alternatively from about 10 microseconds to about 20 milliseconds. Generally, the residence time of a zone or chamber refers to the average amount of time that a compound (e.g., a molecule of that compound) spends in that particular zone or chamber. In an aspect, the ANJEVOC 100 can be characterized by a residence time effective to allow for the conversion of at least a portion of the cracking feed (e.g., hydrocarbons in stream 10) to ethylene. In some aspects, the ANJEVOC 100 may be characterized by a residence time that may range from less than about 20, 19, 18, 17, 16, 15, 14, 13, 12, 11, or 10 milliseconds to about 10 microseconds.

The reaction temperature within the cracking zone of the ANJEVOC 100 may range from about 700° C. to about 1,300° C., alternatively from about 800° C. to about 1,300° C., alternatively from about 900° C. to about 1,300° C., alternatively from about 1,000° C. to about 1,300° C., alternatively from about 1,200° C. to about 1,250° C., or alternatively from about 850° C. to about 1,100° C. The cracking zone temperatures that can be achieved within the ANJEVOC are higher than the temperatures that can be achieved in conventional cracking reactors, such as tube furnace reactors, which typically operate at 800° C.-900° C., owing to the temperature limitations of the metallic materials used for such conventional reactors. In the ANJEVOC, the swirling gas mixture facilitates keeping the walls of the ANJEVOC much cooler than in conventional reactors, wherein the swirling gas mixture allows for the higher cracking temperatures to concentrate in the center of the cracking zone, away from the ANJEVOC walls. The use of such higher temperatures in the cracking zone of the ANJEVOC may also allow for shorter residence times in the ANJEVOC when compared to conventional crackers, wherein the shorter residence times in the ANJEVOC may result in better selectivity and conversion without formation of unwanted products, when compared to cracking in conventional reactors. As will be appreciated by one of skill in the art, and with the help of this disclosure, operating temperatures for the cracking zone of the ANJEVOC may be selected to avoid excess production of unwanted compounds, such as acetylene. As will be appreciated by one of skill in the art, and with the help of this disclosure, higher temperatures in the cracking zone favor alkyne (e.g., acetylene) formation, while lower temperatures in the cracking zone favor olefin or alkene (e.g., ethylene) formation.

The ANJEVOC and its operation are described in more detail in Publication Nos. WO 2019/173570 A1, and WO 2020/086681 A2; each of which is incorporated by reference herein in its entirety.

The cracking product 20 may be removed or discharged from the cracking zone of the ANJEVOC 100 via the ANJEVOC outlet. The cracking product 20 may comprise ethylene, acetylene, ethane, methane, water, $CO_2$, CO, hydrogen, and oxygenates. The cracking product 20 may further comprise $C_{3+}$ hydrocarbons. Since the ANJEVOC 100 combines both the fuel combustion and hydrocarbon cracking in the same chamber, the cracking product 20 contains a significant amount of CO, $CO_2$, and water; regardless of the type of hydrocarbons used in the cracking feed (e.g., hydrocarbons 10).

In an aspect, water may be present in the cracking product 20 in an amount of from about 10 wt. % to about 60 wt. %, alternatively from about 20 wt. % to about 60 wt. %, alternatively from about 10 wt. % to about 55 wt. %, alternatively from about 20 wt. % to about 55 wt. %, alternatively from about 30 wt. % to about 55 wt. %, alternatively from about 40 wt. % to about 55 wt. %, alternatively from about 30 wt. % to about 50 wt. %, or alternatively from about 40 wt. % to about 50 wt. %, based on the total weight of the cracking product 20. For example, water may be present in the cracking product 20 in an amount that is from about 5 to about 50 times, alternatively from about 15 to about 35 times, or alternatively from about 23 to about 28 times greater than the amount of water in a cracking effluent produced by using a substantially similar cracking feed in a conventional hydrocarbon cracker.

In an aspect, oxygenates may be present in the cracking product 20 in an amount of from about 0.07 wt. % to about 1 wt. %, alternatively from about 0.07 wt. % to about 0.85 wt. %, alternatively from about 0.07 wt. % to about 0.7 wt. %, alternatively from about 0.1 wt. % to about 1 wt. %, alternatively from about 0.1 wt. % to about 0.85 wt. %, alternatively from about 0.1 wt. % to about 0.7 wt. %, or alternatively from about 0.15 wt. % to about 0.6 wt. %, based on the total weight of the cracking product 20. For example, oxygenates may be present in the cracking product 20 in an amount that is equal to or greater than about 100 times, alternatively equal to or greater than about 50 times, or alternatively equal to or greater than about 10 times greater than the amount of oxygenates in a cracking effluent produced by using a substantially similar cracking feed in a conventional hydrocarbon cracker. Oxygenates may include but are not limited to aldehydes, methanol, ethenone, acetaldehyde, ethylene oxide, and the like, or combinations thereof.

In an aspect, $CO_2$ may be present in the cracking product 20 in an amount of from about 0.5 wt. % to about 10 wt. %, alternatively from about 1 wt. % to about 10 wt. %, or alternatively from about 1 wt. % to about 7 wt. %, based on the total weight of the cracking product 20. For example, $CO_2$ may be present in the cracking product 20 in an amount that is equal to or greater than about 200 times, alternatively equal to or greater than about 100 times, or alternatively equal to or greater than about 50 times greater than the amount of $CO_2$ in a cracking effluent produced by using a substantially similar cracking feed in a conventional hydrocarbon cracker.

In an aspect, CO may be present in the cracking product 20 in an amount of from about 0.5 wt. % to about 10 wt. %, alternatively from about 0.5 wt. % to about 7.5 wt. %, alternatively from about 0.5 wt. % to about 5 wt. %, alternatively from about 1 wt. % to about 5 wt. %, or alternatively from about 1 wt. % to about 4 wt. %, based on the total weight of the cracking product 20. For example, CO may be present in the cracking product 20 in an amount that is equal to or greater than about 50 times, alternatively equal to or greater than about 25 times, or alternatively equal to or greater than about 10 times greater than the amount of CO in a cracking effluent produced by using a substantially similar cracking feed in a conventional hydrocarbon cracker.

In an aspect, acetylene may be present in the cracking product 20 in an amount of from about 1 wt. % to about 25 wt. %, alternatively from about 5 wt. % to about 20 wt. %, or alternatively from about 2.5 wt. % to about 17.5 wt. %, based on the total weight of the cracking product 20. For example, acetylene may be present in the cracking product 20 in an amount that is equal to or greater than about 10 times, alternatively equal to or greater than about 5 times, or alternatively equal to or greater than about 2 times greater than the amount of acetylene in a cracking effluent produced by using a substantially similar cracking feed in a conventional hydrocarbon cracker.

In an aspect, hydrogen may be present in the cracking product 20 in an amount of from about 0.5 wt. % to about 10 wt. %, alternatively from about 1 wt. % to about 5 wt. %, or alternatively from about 1 wt. % to about 4 wt. %, based on the total weight of the cracking product 20.

In an aspect, methane may be present in the cracking product 20 in an amount of from about 1 wt. % to about 12.5 wt. %, alternatively from about 1.5 wt. % to about 10 wt. %, or alternatively from about 2 wt. % to about 8 wt. %, based on the total weight of the cracking product 20.

In an aspect, ethane may be present in the cracking product 20 in an amount of from about 1 wt. % to about 20 wt. %, alternatively from about 2 wt. % to about 17.5 wt. %, or alternatively from about 2.5 wt. % to about 15 wt. %, based on the total weight of the cracking product 20.

In an aspect, ethylene may be present in the cracking product 20 in an amount of from about 10 wt. % to about 40 wt. %, alternatively from about 20 wt. % to about 40 wt. %, alternatively from about 21 wt. % to about 35 wt. %, or alternatively from about 22.5 wt. % to about 30 wt. %, based on the total weight of the cracking product 20.

In an aspect, the cracking product 20 can be characterized by a first cracking product temperature of from about 700° C. to about 1,300° C., alternatively from about 800° C. to about 1,300° C., alternatively from about 900° C. to about 1,300° C., alternatively from about 1,000° C. to about 1,300° C., alternatively from about 1,200° C. to about 1,250° C., or alternatively from about 850° C. to about 1,100° C. The temperature of the cracking zone effluent (e.g., first cracking product temperature) can be substantially the same as the reaction temperature within the cracking zone, owing to the relatively short residence times in the ANJEVOC 100. Suppression or reduction of reactions leading to products other than the desired products (e.g., olefins, ethylene) may be required to achieve the desired products. In some aspects, suppression or reduction of reactions leading to products other than the desired products may be accomplished by relatively rapid cooling of the cracking product 20 after a desired residence time (e.g., quenching of ANJEVOC effluent).

In an aspect, a process for producing ethylene as disclosed herein can comprise a step of cooling at least a portion of the cracking product 20 in a first cracking product cooling zone 210 to yield a first cooled cracking product 22; wherein the first cooled cracking product 22 is characterized by a second cracking product temperature; and wherein the second cracking product temperature is lower than the first cracking product temperature.

In some aspects, in order to terminate side reactions resulting in undesired products from occurring in the cracking product 20, prevent undesired reverse reactions in the cracking product 20, and/or prevent further reactions that form carbon and hydrocarbon compounds other than the desired products (e.g., olefins, ethylene); rapid cooling or "quenching" of the cracking zone effluent (e.g., cracking product 20) can be employed, for example in the first cracking product cooling zone or quench zone 210.

In an aspect, the first cracking product cooling zone 210 can be characterized by a residence time of less than about 2,000 milliseconds, alternatively less than about 1,000 milliseconds, alternatively less than about 500 milliseconds, alternatively less than about 250 milliseconds, or alternatively less than about 100 milliseconds.

In some aspects, a reactor may contain both the ANJEVOC 100 and the quench zone 210; wherein the quench zone is downstream of the cracking zone of the ANJEVOC 100. In other aspects, the process for producing ethylene as disclosed herein may employ an ANJEVOC reactor 100 that discharges an ANJEVOC effluent (e.g., cracking product 20) into a cooling unit or section comprising the first cracking product cooling zone or quench zone 210, wherein the cooling unit comprising the quench zone 210 is immediately downstream of the ANJEVOC reactor 100.

The first cracking product cooling zone or quench zone 210 can employ any suitable quenching methods, for example spraying a quench fluid such as steam, water, oil, or liquid product into the quench zone; conveying the cracking zone effluent (e.g., cracking product 20) through or into water, hydrocarbon feed, or liquid products; preheating other process streams such as the fuel gas stream 15 and/or the hydrocarbon stream 10; generating steam, such as steam stream 16; expanding in a kinetic energy quench, such as a Joule Thompson expander, choke nozzle, turbo expander, etc.; or combinations thereof. The first cracking product cooling zone or quench zone 210 may be incorporated within the ANJEVOC reactor 100, may comprise a separate vessel or device from the ANJEVOC reactor 100, or both. In some aspects, water (e.g., quench water stream 21) can be used to quench the cracking zone effluent (e.g., cracking product 20), for example as depicted in FIGS. 1 and 2, where a water quench spray is employed to achieve rapid cooling of the ANJEVOC effluent.

In an aspect, the step of cooling at least a portion of the cracking product 20 in a first cracking product cooling zone 210 comprises direct water quench; wherein the direct water quench comprises contacting at least a portion of the cracking product 20 with quench water 21 to yield the first cooled cracking product 22; wherein the first cooled cracking product 22 comprises ethylene, acetylene, ethane, methane, $CO_2$, CO, hydrogen, oxygenates, at least a portion of the water of the cracking product 20, and at least a portion of the quench water 21.

In an aspect, the direct water quench may comprise contacting at least a portion of the cracking product 20 with quench water 21 having a temperature of from about 5° C. to about 90° C., alternatively from about 10° C. to about 40° C., alternatively from about 20° C. to about 70° C., alternatively from about 30° C. to about 90° C., or alternatively from about 30° C. to about 50° C.; and wherein the first cooled cracking product 22 comprises the quench water in an amount of from about 1 wt. % to about 10 wt. %, alternatively from about 2 wt. % to about 9 wt. %, or alternatively from about 2.5 wt. % to about 8 wt. %, based on the total weight of the first cooled cracking product 22. In aspects where the rapid cooling of the cracking product 20 occurs via direct heat exchange (e.g., direct water quench), the first cooled cracking product 22 will contain the heat exchange medium used for the direct heat exchange (e.g., quench water 21). In aspects where the rapid cooling of the cracking product 20 occurs via indirect heat exchange, the first cooled cracking product 22 will have substantially the same composition as the cracking product 20, but a lower temperature than the cracking product 20.

In an aspect, the difference between the first cracking product temperature and the second cracking product temperature can be equal to or greater than about 30° C., alternatively equal to or greater than about 40° C., or alternatively equal to or greater than about 50° C.

In an aspect, the second cracking product temperature can be less than about 900° C., alternatively less than about 875° C., alternatively less than about 850° C., alternatively less than about 825° C., or alternatively less than about 800° C. In an aspect, the second cracking product temperature can be a temperature effective for (e.g., the highest temperature effective for) substantially reducing or terminating side reactions resulting in undesired products from occurring in the cracking product 20. The higher the second cracking product temperature, the more heat can be recovered from the first cooled cracking product 22 in the cracking product heat exchanger 220. The cracking product 20 can be rapidly cooled by direct heat exchange in a quench zone 210 (to reduce or eliminate undesired side reactions) before being further cooled by indirect heat exchange in a heat exchanger such as a transfer line exchanger (TLE) 220 (to recover heat).

In an aspect, a process for producing ethylene as disclosed herein can comprise a step of cooling at least a portion of the first cooled cracking product 22 in a heat exchanger 220 (e.g., cracking product heat exchanger unit 220) to yield a second cooled cracking product 25; wherein the second cooled cracking product 25 is characterized by a third cracking product temperature; wherein the third cracking product temperature is lower than the second cracking product temperature; and wherein cooling at least a portion of the first cooled cracking product 22 comprises cooling at least a portion of the first cooled cracking product 22 while heating a heat exchange medium in the cracking product heat exchanger 220 to yield the second cooled cracking product 25 and a heated heat exchange medium, respectively. The first cooled cracking product 22 can exchange heat with feed streams to the ANJEVOC 100 (e.g., streams 10, 11, 15, 16) to increase a temperature of the feed streams, while decreasing the temperature of the cracking product.

In some aspects, the heat exchange medium comprises fuel gas (e.g., stream 15) and/or hydrocarbons (e.g., stream 10); wherein the heated heat exchange medium comprises heated fuel gas and/or heated hydrocarbons, respectively; and wherein at least a portion of the heated fuel gas and/or at least a portion of the heated hydrocarbons are introduced to the ANJEVOC 100. In such aspects, the heat exchanger 220 and the heat exchangers 101, 102 can be the same heat exchanger where the cracking product effluent exchanges heat with the hydrocarbons to increase the temperature of the hydrocarbons, while decreasing the temperature of the cracking product. In other aspects, the heat exchanger 220 and the heat exchangers 101, 102 can be different heat exchangers.

In some aspects, the heat exchange medium comprises water (e.g., removed water, such as stream 31a); wherein the heated heat exchange medium comprises steam (e.g., stream 34); and wherein at least a portion (34a) of the steam is optionally introduced to the ANJEVOC 100. In such aspects, the heat exchanger 220 and the heat exchanger 330 can be the same heat exchanger where the cracking product effluent exchanges heat with the removed water to increase the temperature of the water and produce steam, while decreasing the temperature of the cracking product. In other aspects, the heat exchanger 220 and the heat exchanger 330 can be different heat exchangers.

In an aspect, the difference between the second cracking product temperature and the third cracking product temperature can be equal to or greater than about 300° C., alternatively equal to or greater than about 450° C., or alternatively equal to or greater than about 600° C. The greater the difference between the second cracking product temperature and the third cracking product temperature, the more heat is being recovered in the heat exchanger 220 from the cracking product.

In an aspect, the third cracking product temperature can be less than about 350° C., alternatively less than about 300° C., or alternatively less than about 250° C. The second cooled cracking product 25 has substantially the same composition as the first cooling cracking product 22.

In an aspect, a process for producing ethylene as disclosed herein can comprise a step of separating at least a portion of the second cooled cracking product 25 into a cracked gas 27 and removed water 26; wherein the removed water 26 comprises at least a portion of the water of the cracking product 20; wherein the removed water 26 comprises at least a portion of the oxygenates of the cracking product 20; and wherein the cracked gas 27 comprises ethylene, acetylene, ethane, methane, $CO_2$, CO, and hydrogen. For example, at least a portion of the second cooled cracking product 25 can be introduced to a quench tower 250, wherein the second cooled cracking product 25 can be sprayed with quench water and/or quench oil (e.g., stream 32) to remove the water in the cracking product and allow for the recovery of the cracked gas 27. The recovered cracked gas 27 may be further cooled in a water quench tower to a temperature of less than about 50° C., alternatively less than about 40° C., or alternatively less than about 37° C. to reduce volumetric flow to the one or more cracked gas compressors 370. In some aspects, the second cooled cracking product 25 and the quench water and/or quench oil (e.g., stream 32) can be introduced countercurrent to the quench tower 250.

In some aspects, a fuel oil 30 can further be recovered from the removed water 26, wherein the fuel oil comprises $C_8$-$C_{30}$ hydrocarbons. Stream 30 can be recovered from stream 26 in separator 310, to produce a removed water 31. In some aspects, a portion 31b of the removed water (e.g., a third portion of the removed water 31) can be cooled in heat exchanger 320 to yield stream 32, wherein stream 32 can be used to quench the second cooled cracking product 25 in the quench tower 250, as described herein.

In some aspects, a portion 31a of the removed water can be further sent to water treatment and/or steam production.

In an aspect, a first portion 33 of the removed water can be converted to steam 34, for example in heat exchanger 330, wherein at least a portion of steam 34 can be used for diluting the fuel gas 15 and/or hydrocarbons 10 in the ANJEVOC 100.

In an aspect, a second portion 35 of the removed water can be introduced to a WWT unit or section 300 to yield treated water 36; wherein the removed water 31a, 31, 35 is characterized by a first amount of oxygenates; wherein the treated water 36 is characterized by a second amount of oxygenates; and wherein a weight ratio of the first amount of oxygenates to the second amount of oxygenates is equal to or greater than about 10, alternatively equal to or greater than about 20, or alternatively equal to or greater than about 25. The WWT unit 300 processes a relatively large amount of water (for example when compared to the amount of water in a cracking effluent produced by using a substantially similar cracking feed in a conventional hydrocarbon cracker). Further, the WWT unit 300 processes water containing a relatively large amount of oxygenates (for example when compared to the amount of oxygenates in a cracking effluent produced by using a substantially similar cracking feed in a conventional hydrocarbon cracker). Therefore, the WWT unit 300 for treating the water removed from the ANJEVOC effluent includes multiple steps of chemical, physical and biological wastewater treatment.

In an aspect, a process for producing ethylene as disclosed herein can comprise a step of introducing at least a portion of the cracked gas 27 to a continuous regeneration $CO_2$ removal unit 400 to produce a $CO_2$-lean cracked gas 41. In some aspects, at least a portion of the cracked gas 27 can be compressed in one or more cracked gas compressors 370 to produce a compressed cracked gas 37; wherein at least a portion of the compressed cracked gas 37 can be introduced to the continuous regeneration $CO_2$ removal unit 400 to produce the $CO_2$-lean cracked gas 41. In some aspects, at least a portion of the cracked gas 27 and/or at least a portion of the compressed cracked gas 37 can be further cooled in heat exchanger 380 to yield a cooled cracked gas 38; wherein at least a portion of the cooled cracked gas 38 can be introduced to the continuous regeneration $CO_2$ removal unit 400 to produce the $CO_2$-lean cracked gas 41. In an aspect, the continuous regeneration $CO_2$ removal unit 400 may employ a solvent (e.g., amine, methanol, or any other suitable solvent) that is continuously introduced to an absorption tower to remove the $CO_2$ from the cracked gas 27 thus producing a spent solvent that may be continuously regenerated in a desorption tower prior to recycling to the absorption tower.

In some aspects, the continuous regeneration $CO_2$ removal unit 400 may comprise $CO_2$ removal by amine (e.g., monoethanolamine) absorption (e.g., amine scrubbing), wherein a $CO_2$-loaded amine solution can be continuously circulated for regeneration (e.g., $CO_2$ desorption, for example by heating the $CO_2$-loaded amine solution) to yield a regenerated amine solution (which may be cooled prior to recirculating for $CO_2$ absorption) and wherein the regenerated amine solution may be continuously contacted with the cracked gas 27 to remove a portion of the $CO_2$ from the cracked gas 27, thereby forming the $CO_2$-loaded amine solution and the $CO_2$-lean cracked gas 41. Fresh amine solution may need to be added to the regenerated amine solution to compensate for amine loss.

In some aspects, the continuous regeneration $CO_2$ removal unit 400 may provide for the removal of equal to or greater than about 80%, alternatively equal to or greater than about 90%, alternatively equal to or greater than about 95%, or alternatively equal to or greater than about 98% of the $CO_2$ present in the cracked gas 27. In an aspect, the cracked gas 27 can be characterized by a first amount of $CO_2$, and the $CO_2$-lean cracked gas 41 can be characterized by a second amount of $CO_2$; wherein a weight ratio of the first amount of $CO_2$ to the second amount of $CO_2$ is equal to or greater than about 5, alternatively equal to or greater than about 10, alternatively equal to or greater than about 20, alternatively equal to or greater than about 30, or alternatively equal to or greater than about 50.

The ANJEVOC effluent (e.g., cracking product 20) contains a significant amount of $CO_2$ (for example when compared to the amount of $CO_2$ in a cracking effluent produced by using a substantially similar cracking feed in a conventional hydrocarbon cracker) and a continuous regeneration unit (e.g., continuous regeneration $CO_2$ removal unit 400) is needed to remove the bulk of $CO_2$ from the cracked gas, followed by a once-through unit to further reduce the $CO_2$ to a relatively low concentration. The effluent from conventional hydrocarbon cracker do not contain a significant amount of $CO_2$ and a once-through system is generally sufficient for $CO_2$ removal.

In an aspect, a process for producing ethylene as disclosed herein can comprise a step of introducing at least a portion of the $CO_2$-lean cracked gas 41 to a once-through $CO_2$ removal unit 450 to produce a $CO_2$-depleted cracked gas 46; wherein the $CO_2$-depleted cracked gas 46 comprises ethylene, acetylene, ethane, methane, CO, and hydrogen. The once-through $CO_2$ removal unit 450 may be a caustic tower, wherein a caustic solution is introduced to the caustic tower along with the $CO_2$-lean cracked gas 41 (for example countercurrent with the $CO_2$-lean cracked gas 41), wherein at least a portion of the $CO_2$ in the $CO_2$-lean cracked gas 41 is absorbed by the caustic solution to produce the $CO_2$-depleted cracked gas 46 and a spent caustic stream 45. A portion 45b of the spent caustic stream may be discarded (following appropriate treatment to neutralize the solution). A portion 45a of the spent caustic may be optionally contacted with water and/or fresh caustic and may be recycled to the caustic tower.

In an aspect, the $CO_2$-depleted cracked gas 46 is substantially free of $CO_2$. In an aspect, the $CO_2$-depleted cracked gas 46 comprises $CO_2$ in an amount of less than about 100 ppmw, alternatively less than about 50 ppmw, alternatively less than about 25 ppmw, alternatively less than about 10 ppmw, alternatively less than about 7.5 ppmw, or alternatively less than about 5 ppmw, based on the total weight of the $CO_2$-depleted cracked gas 46. In aspects where the cracking product 20 comprises $C_{3+}$ hydrocarbons, the $CO_2$-depleted cracked gas 46 comprises $C_{3+}$ hydrocarbons, such as $C_3$ hydrocarbons (e.g., propane, propylene), $C_4$ hydrocarbons (e.g., butane, butylene, butadiene), $C_5$ hydrocarbons (e.g., pentane, pentene), etc.

In some aspects, at least a portion of the $CO_2$-depleted cracked gas 46 may be further cooled in heat exchanger 460 to yield a cooled $CO_2$-depleted cracked gas 47, in order to facilitate the further separation of the $CO_2$-depleted cracked gas into its components. Individual hydrocarbons or hydrocarbon fractions can be usually recovered from the $CO_2$-depleted cracked gas 46 and/or cooled $CO_2$-depleted cracked gas 47 by fractionation processes that can employ a variety of distillation columns; e.g., cryogenic distillation columns comprising a demethanizer 510, a deethanizer 520, a depropanizer 530, a debutanizer 540, a $C_2$ splitter 550, etc. Thus cooling a gas stream (e.g., $CO_2$-depleted cracked gas 46) may be beneficial prior to hydrocarbons recovery via cryogenic fractionation processes.

In an aspect, for example as depicted in the configuration of system 1000 in FIG. 1, a process for producing ethylene as disclosed herein can comprise separating in the deethanizer 520 at least a portion of the $CO_2$-depleted cracked gas 46 and/or at least a portion of the cooled $CO_2$-depleted cracked gas 47 into a $C_{2-}$ hydrocarbons stream 69 and a $C_{3+}$ hydrocarbons stream 53; wherein the $C_{2-}$ hydrocarbons stream 69 comprises ethylene, acetylene, ethane, methane, CO, and hydrogen; and wherein the $C_{3+}$ hydrocarbons stream 53 comprises $C_{3+}$ hydrocarbons.

In an aspect, at least a portion of the $C_{3+}$ hydrocarbons stream 53 can be introduced to the debutanizer 540 to yield a $C_{4-}$ hydrocarbons stream 76 and a $C_{5+}$ hydrocarbons stream 58; wherein the $C_{4-}$ hydrocarbons stream 76 comprises $C_3$ hydrocarbons and $C_4$ hydrocarbons; and wherein the $C_{5+}$ hydrocarbons stream 58 comprises and $C_{5+}$ hydrocarbons.

In an aspect, at least a portion of the $C_{4-}$ hydrocarbons stream 76 can be introduced to the depropanizer 530 to yield a $C_3$ hydrocarbons stream 55 and a $C_4$ hydrocarbons stream 59; wherein the $C_3$ hydrocarbons stream 55 comprises $C_3$ hydrocarbons; and wherein the $C_4$ hydrocarbons stream 59 comprises and $C_4$ hydrocarbons. The debutanizer 540 and the depropanizer 530 can switch their sequence and still maintain the same separation performance, or they can be removed (e.g., omitted) when there is no need to have relatively pure $C_3$ and/or $C_4$ hydrocarbon products.

In an aspect, a process for producing ethylene as disclosed herein can further comprise compressing at least a portion of the $C_{2-}$ hydrocarbons stream 69 (e.g., via compressor(s) 521) to yield a compressed $C_{2-}$ hydrocarbons stream 69c prior to introducing the $C_{2-}$ hydrocarbons to the acetylene converter 500. In some aspects, at least a portion of water traces can be removed from the compressed $C_{2-}$ hydrocarbons stream 69c to yield a dehydrated $C_{2-}$ hydrocarbons stream, wherein the dehydrated $C_{2-}$ hydrocarbons stream is introduced to the acetylene converter 500. Generally, compressing a gas that contains water from a first pressure to a second pressure (wherein the second pressure is greater than the first pressure) will lead to the water condensing at the second pressure at an increased temperature as compared to a temperature where water of an otherwise similar gas condenses at the first pressure. Thus, compressing the $C_{2-}$ hydrocarbons stream 69 may facilitate water removal from the $C_{2-}$ hydrocarbons stream 69. In some aspects, at least a portion of the water can be removed from the $C_{2-}$ hydrocarbons stream 69 and/or compressed $C_{2-}$ hydrocarbons stream 69c by using molecular sieves. The $C_{2-}$ hydrocarbons stream 69 and/or compressed $C_{2-}$ hydrocarbons stream 69c can be further cooled in a cooling unit (e.g., heat exchanger) to promote water condensation and removal, thereby yielding the dehydrated $C_{2-}$ hydrocarbons stream.

In an aspect, at least a portion of the $C_{2-}$ hydrocarbons stream 69, at least a portion of the compressed $C_{2-}$ hydrocarbons stream 69c, at least a portion of the dehydrated $C_{2-}$ hydrocarbons stream, or combinations thereof can be introduced to the acetylene converter 500 to yield an ethylene-enriched $C_{2-}$ hydrocarbons stream 60; wherein the ethylene-enriched $C_{2-}$ hydrocarbons stream 60 comprises ethylene, ethane, methane, CO, and hydrogen; and wherein an amount of ethylene in the ethylene-enriched $C_{2-}$ hydrocarbons stream 60 is greater than the amount of ethylene in the $C_{2-}$ hydrocarbons stream 69, the compressed $C_{2-}$ hydrocarbons stream 69c, the dehydrated $C_{2-}$ hydrocarbons stream, or combinations thereof, respectively.

The acetylene converter 500 can comprise any suitable the acetylene converter that can selectively hydrogenate acetylene to ethylene, while avoiding hydrogenating ethylene. In some aspects, the acetylene converter 500 can comprise any suitable liquid phase hydrogenation reactor, such as a fixed bed catalytic reactor (typically operated adiabatically); and/or a tubular reactor (typically operated isothermally). Generally, a liquid phase hydrogenation reactor may comprise a hydrogenation catalyst, such as a palladium based catalyst, which can be supported on alumina, zeolites, etc. The hydrogenation catalyst can further comprise other metals, such as platinum, silver, nickel, etc. In some aspects, the liquid phase hydrogenation reactor can be characterized by a pressure of from about 50 psia to about 200 psia, alternatively from about 75 psia to about 175 psia, or alternatively from about 100 psia to about 160 psia; and/or by a temperature of from about 200° F. to about 400° F., alternatively from about 250° F. to about 375° F., or alternatively from about 300° F. to about 350° F. Liquid phase hydrogenation processes for the conversion of acetylene to ethylene are described in more detail in U.S. Patent Application No. 2010/0152034 A1; which is incorporated by reference herein in its entirety.

In an aspect, for example as depicted in the configuration of system 1000 in FIG. 1, a process for producing ethylene as disclosed herein can comprise separating at least a portion of the ethylene-enriched $C_{2-}$ hydrocarbons stream 60 into one or more $C_{2-}$ hydrocarbons stream(s) 62, 63, 66; and a tail gas stream 70; wherein the $C_{2-}$ hydrocarbons stream(s) 62, 63, 66 comprise methane, ethane, and ethylene; and wherein the tail gas stream 70 comprises hydrogen, CO, and methane. In an aspect, for example as depicted in the configuration of system 1000 in FIG. 1, the separation of the ethylene-enriched $C_{2-}$ hydrocarbons stream 60 can be carried out by employing cold box unit 600; separators 602, 604; and heat exchangers 601, 602. Generally, a cold box system, such as cold box unit 600, may comprise one or more expanders, one or more heat exchangers, and one or more flash units arranged in an any suitable configuration (e.g., series and/or parallel).

In an aspect, at least a portion of the $C_{2-}$ hydrocarbons stream 66 may be recycled to the acetylene converter 500, for example via compressor 521 and the compressed $C_{2-}$ hydrocarbons stream 69c. In an aspect, a portion of the $C_{2-}$ hydrocarbons stream 62 may be recycled to the deethanizer 520.

In an aspect, at least portion of the $C_{2-}$ hydrocarbons streams 62, 63 may be introduced to the demethanizer 510 to yield a methane stream 65 and a $C_2$ hydrocarbons stream 75; wherein the methane stream 65 comprises methane, ethane and ethylene; and wherein the $C_2$ hydrocarbons stream 75 comprises ethylene and ethane. In an aspect, at least a portion of the methane stream 65 may be recycled to the acetylene converter 500, for example via compressor 521 and the compressed $C_{2-}$ hydrocarbons stream 69c.

In an aspect, at least portion of the $C_2$ hydrocarbons stream 75 may be introduced to the $C_2$ splitter 550 to yield ethylene 56 and ethane 57. In an aspect, stream 56 may comprise ethylene in a an amount of equal to or greater than about 99 mol %, alternatively equal to or greater than about 99.5 mol %, or alternatively equal to or greater than about 99.9 mol %.

In an aspect, for example as depicted in the configuration of system 2000 in FIG. 2, a process for producing ethylene as disclosed herein can comprise separating at least a portion of the $CO_2$-depleted cracked gas 46 and/or at least a portion of the cooled $CO_2$-depleted cracked gas 47 into the tail gas 70 and a $C_{2+}$ hydrocarbons stream 52; wherein the $C_{2+}$ hydrocarbons stream 52 comprises $C_{2+}$ hydrocarbons. In such aspect, the separation of the $CO_2$-depleted cracked gas 46 and/or the cooled $CO_2$-depleted cracked gas 47 can be carried out by employing cold box unit 600; separator 470; and demethanizer 510.

In an aspect, at least a portion of the $C_{2+}$ hydrocarbons stream 52 can be introduced to the deethanizer 520 to yield the $C_{3+}$ hydrocarbons stream 53 and a $C_2$ hydrocarbons stream 77; wherein the $C_2$ hydrocarbons stream 77 comprises ethylene, acetylene, and ethane.

In an aspect, at least a portion of the $C_{3+}$ hydrocarbons stream 53 can be introduced to the depropanizer 530 to yield the $C_3$ hydrocarbons stream 55 and a $C_{4+}$ hydrocarbons stream 54; wherein the $C_{4+}$ hydrocarbons stream 54 comprises $C_{4+}$ hydrocarbons.

In an aspect, at least a portion of the $C_{4+}$ hydrocarbons stream 54 can be introduced to the debutanizer 540 to yield the $C_4$ hydrocarbons stream 59 and the $C_{5+}$ hydrocarbons stream 58.

In an aspect, a process for producing ethylene as disclosed herein can further comprise expanding at least a portion of the $C_2$ hydrocarbons stream 77 (e.g., via expander(s) 522) to yield an expanded $C_2$ hydrocarbons stream 77e prior to introducing the $C_2$ hydrocarbons to the acetylene converter 500. Generally, the purpose of such an expansion (e.g., expanding at least a portion of the $C_2$ hydrocarbons stream 77) is to further decrease the temperature of the $C_2$ hydrocarbons stream 77, which then can be used for heat exchange with other high temperature streams. However, the expanded $C_2$ hydrocarbons stream should still maintain a high enough pressure required by the downstream acetylene conversion.

In an aspect, at least a portion of the $C_2$ hydrocarbons stream 77 and/or at least a portion of the expanded $C_2$ hydrocarbons stream 77e can be introduced to the acetylene converter 500 to yield a $C_2$ hydrocarbons stream 50; wherein the $C_2$ hydrocarbons stream 50 comprises ethylene, and ethane. In an aspect, at least portion of the $C_2$ hydrocarbons stream 50 may be introduced to the $C_2$ splitter 550 to yield ethylene 56 and ethane 57.

In an aspect, a process for producing ethylene as disclosed herein can comprise a step of introducing at least a portion of the tail gas 70 to a CO rejection unit 700 to produce a CO-lean gas 71 and a CO-rich gas 72; wherein the CO-lean gas 71 comprises methane, CO, and hydrogen; and wherein an amount of CO in the CO-lean gas 71 is lower than an amount of CO in the tail gas 70. The CO-rich gas 72 comprises methane, CO, and hydrogen; wherein an amount of CO in the CO-rich gas 72 is greater than an amount of CO in the tail gas 70. The CO rejection unit 700 can be a single unit or a combination of two or more units; wherein the CO rejection unit 700 may comprise any suitable unit that can separate carbon monoxide from other light components such as hydrogen and methane; e.g., a membrane separation unit, a pressure swing absorption unit, a distillation unit, and the like, or combinations thereof.

In an aspect, at least a portion 71a of the CO-lean gas can be recycled to the ANJEVOC 100, for example via stream 15. The use of the CO rejection unit 700 advantageously allows for removing a portion of the CO from the tail gas 70 prior to recycling to the ANJEVOC 100, thus preventing the build-up of CO in the recycle loop.

The ANJEVOC effluent (e.g., cracking product 20) contains a significant amount of CO (for example when compared to the amount of CO in a cracking effluent produced by using a substantially similar cracking feed in a conventional hydrocarbon cracker) and a CO rejection unit (e.g., CO rejection unit 700) is needed to remove the bulk of CO from the tail gas, in order to recycle the hydrogen in the tail gas to the ANJEVOC 100, while preventing the build-up of CO in the recycle loop.

In some aspects, the CO-rich gas 72 can be further used as fuel.

In an aspect, a process for producing ethylene as disclosed herein can advantageously display improvements in one or more process characteristics when compared to conventional processes for the production of ethylene with a conventional hydrocarbon cracker. Owing to the design of the ANJEVOC, which is significantly different from conventional hydrocarbon cracker as disclosed herein, the ANJEVOC effluent is also significantly different in composition and physical properties from cracking effluents produced with conventional hydrocarbon crackers (e.g., conventional ethane steam crackers), even when substantially the same hydrocarbon feed is used. Consequently, conventional separation processes employed for processing effluents from conventional hydrocarbon crackers (e.g., conventional ethane steam crackers) cannot handle the ANJEVOC effluent. For example, since the ANJEVOC advantageously employs both the fuel combustion and hydrocarbon cracking in the same chamber, there are significant amounts of carbon monoxide and carbon dioxide in the ANJEVOC effluent. However, the conventional hydrocarbon crackers are generally designed to employ indirect heat supply and there are no significant amounts of carbon monoxide and carbon dioxide in the effluent from the conventional hydrocarbon crackers. Further, the conventional separation processes employed for processing effluents from conventional hydrocarbon crackers (e.g., conventional ethane steam crackers) are not designed to process streams having elevated temperatures, such as a temperature of from about 900° C. to about 1300° C.

In an aspect, the process for producing ethylene as disclosed herein can advantageously process the ANJEVOC effluent having significant amounts of carbon monoxide and carbon dioxide in order to recover ethylene and recycle streams as necessary. In an aspect, the process for producing ethylene as disclosed herein can advantageously process the ANJEVOC effluent having a temperature of from about 900° C. to about 1300° C. Additional advantages of the processes for producing ethylene as disclosed herein can be apparent to one of skill in the art viewing this disclosure.

EXAMPLES

The subject matter having been generally described, the following examples are given as particular embodiments of the disclosure and to demonstrate the practice and advantages thereof. It is understood that the examples are given by way of illustration and are not intended to limit the specification of the claims to follow in any manner.

Example 1

A process for producing ethylene as disclosed herein was investigated. More specifically, a computerized simulation using software, Aspen Plus V10, which is commercially available from AspenTech, was used for investigating a process for ethylene production. Specifically, a front-end selective acetylene hydrogenation process for ethylene production was investigated in accordance with FIG. 1, and the results are displayed in FIG. 3; and a back-end selective acetylene hydrogenation process for ethylene production was investigated in accordance with FIG. 2, and the results are displayed in FIG. 4. The process units in FIGS. 3 and 4 have been labeled corresponding to the process units in FIGS. 1 and 2, respectively. However, for clarity purposes, the streams in FIGS. 3 and 4 have not been labelled with stream numbers corresponding to FIGS. 1 and 2.

The simulations were conducted in each case for a cracking product having the composition and properties displayed in Table 1.

TABLE 1

| | | Cracking product composition (weight fraction) | | | | | | | | | |
|---|---|---|---|---|---|---|---|---|---|---|---|
| T | P | $H_2$ | CO | $CO_2$ | $CH_4$ | $C_2H_2$ | $C_2H_4$ | $C_2H_6$ | Oxygenates | Other hydrocarbons | Water |
| 909° C. | 60 Psig | 0.028 | 0.026 | 0.04 | 0.042 | 0.012 | 0.277 | 0.083 | 0.003 | 0.022 | 0.467 |

Figure 3:
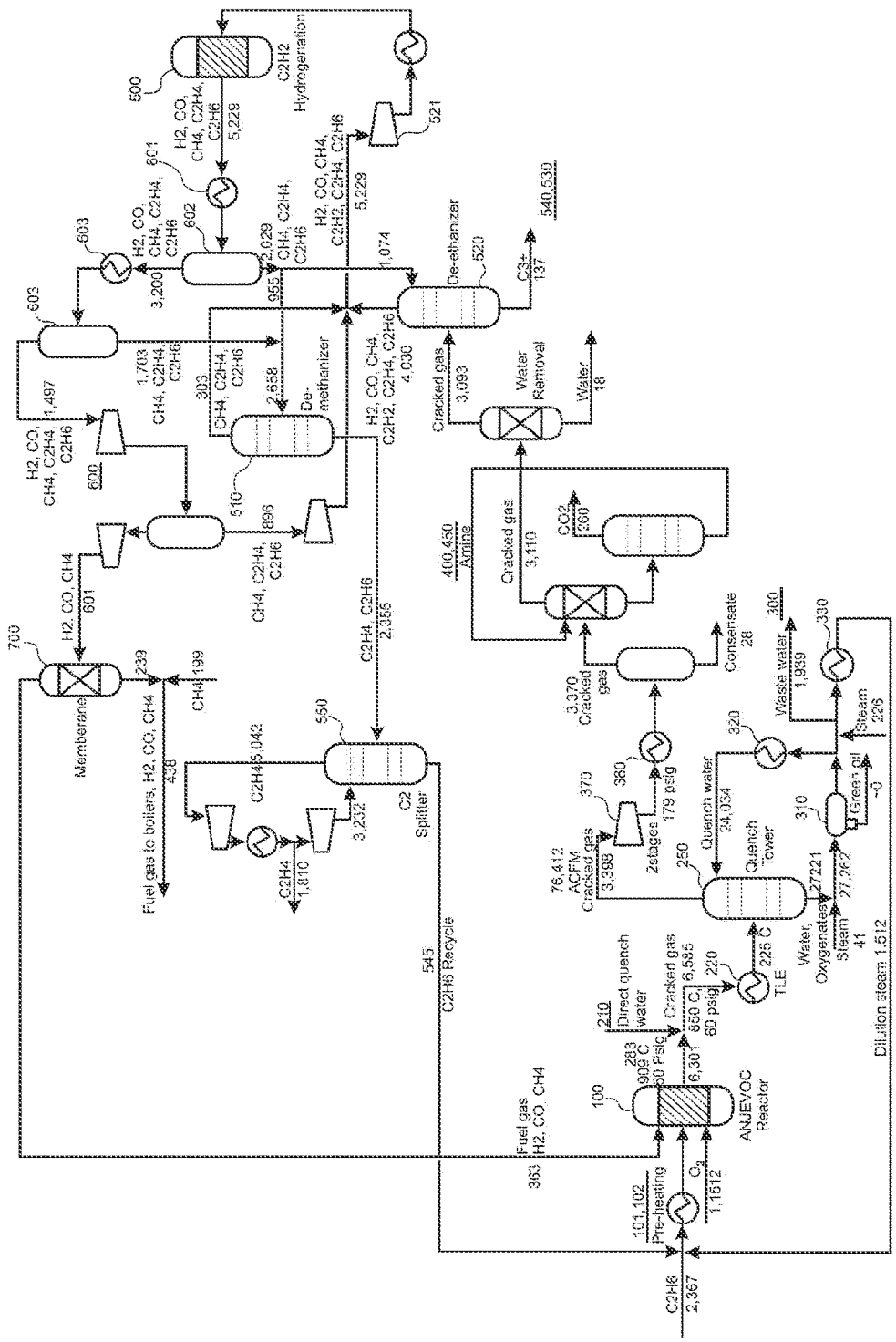
FIG. 3 displays yet another configuration of an ethylene production system.
Figure 4:
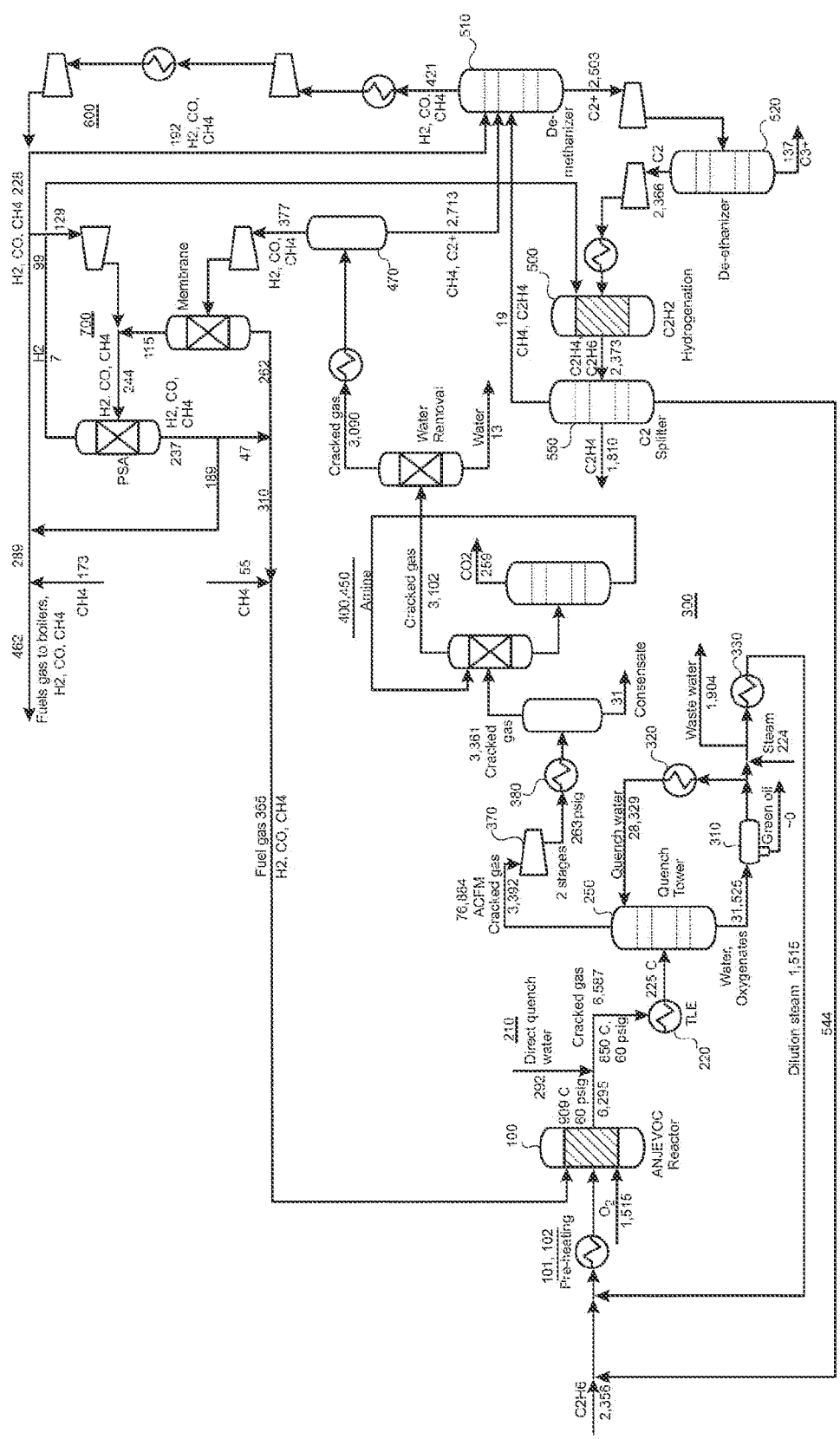
FIG. 4 displays still yet another configuration of an ethylene production system.

The feed in each case is pure ethane. The ethylene recovered in each case had a purity higher than 99.9%, which is targeted as the normal (e.g., conventional) specification of industrial products. FIGS. 3 and 4 provide the detailed mass balance for the entire respective separation process. It should be noted that the numbers shown in FIGS. 3 and 4 represent the mass flow rate of each stream in the unit of 1,000 metric tons per year.

ADDITIONAL DISCLOSURE

The following are non-limiting, specific embodiments in accordance with the present disclosure.

A first aspect, which is a process for producing ethylene comprising (a) introducing a fuel gas, hydrocarbons, an oxidant gas, and steam to an annular jet vortex chamber (ANJEVOC) to provide for a swirling fluid flow pattern within the ANJEVOC; wherein the ANJEVOC comprises a combustion zone and a cracking zone; wherein the combustion zone is upstream of the cracking zone; wherein the oxidant gas does not contact the fuel gas outside of the ANJEVOC; wherein the oxidant gas does not contact the hydrocarbons outside of the ANJEVOC; wherein the hydrocarbons comprise ethane and/or saturated hydrocarbons other than ethane; wherein at least a portion of the fuel gas and at least a portion of the oxidant gas contact each other in the combustion zone to produce a combustion product; wherein the combustion product comprises water and carbon dioxide; wherein the swirling fluid flow pattern provides for conveying at least a portion of the combustion product to the cracking zone; wherein the combustion product heats the hydrocarbons in the cracking zone to a temperature effective for a cracking reaction; and wherein at least a portion of the hydrocarbons undergoes a cracking reaction in the cracking zone to produce a cracking product; wherein the cracking product comprises ethylene, acetylene, ethane, methane, water, carbon dioxide ($CO_2$), carbon monoxide (CO), hydrogen, and oxygenates; wherein water is present in the cracking product in an amount of from about 10 wt. % to about 60 wt. %, based on the total weight of the cracking product; and wherein the cracking product is characterized by a first cracking product temperature; (b) cooling at least a portion of the cracking product in a first cracking product cooling zone to yield a first cooled cracking product; wherein the first cooled cracking product is characterized by a second cracking product temperature; wherein the second cracking product temperature is lower than the first cracking product temperature; wherein the difference between the first cracking product temperature and the second cracking product temperature is equal to or greater than about 30° C.; and wherein the first cracking product cooling zone is characterized by a residence time of less than about 2,000 milliseconds; (c) cooling at least a portion of the first cooled cracking product in a cracking product heat exchanger to yield a second cooled cracking product; wherein the second cooled cracking product is characterized by a third cracking product temperature; wherein the third cracking product temperature is lower than the second cracking product temperature; wherein the difference between the second cracking product temperature and the third cracking product temperature is equal to or greater than about 300° C.; and wherein cooling at least a portion of the first cooled cracking product comprises cooling at least a portion of the first cooled cracking product while heating a heat exchange medium in the cracking product heat exchanger to yield the second cooled cracking product and a heated heat exchange medium, respectively; (d) separating at least a portion of the second cooled cracking product into a cracked gas and removed water; wherein the removed water comprises at least a portion of the water of the cracking product; wherein the removed water comprises at least a portion of the oxygenates of the cracking product; and wherein the cracked gas comprises ethylene, acetylene, ethane, methane, $CO_2$, CO, and hydrogen; (e) introducing at least a portion of the cracked gas to a continuous regeneration $CO_2$ removal unit to produce a $CO_2$-lean cracked gas; wherein the cracked gas is characterized by a first amount of $CO_2$; wherein the $CO_2$-lean cracked gas is characterized by a second amount of $CO_2$; and wherein a weight ratio of the first amount of $CO_2$ to the second amount of $CO_2$ is equal to or greater than about 5; (f) introducing at least a portion of the $CO_2$-lean cracked gas to a once-through $CO_2$ removal unit to produce a $CO_2$-depleted cracked gas; wherein the $CO_2$-depleted cracked gas comprises ethylene, acetylene, ethane, methane, CO, and hydrogen; and (g) separating at least a portion of the $CO_2$-depleted cracked gas into ethylene, ethane, and a tail gas; wherein the tail gas comprises methane, CO, and hydrogen.

A second aspect, which is the process of the first aspect, wherein the step (b) of cooling at least a portion of the cracking product in a first cracking product cooling zone comprises direct water quench; wherein the direct water quench comprises contacting at least a portion of the cracking product with quench water to yield the first cooled cracking product; wherein the first cooled cracking product comprises ethylene, acetylene, ethane, methane, $CO_2$, CO, hydrogen, oxygenates, at least a portion of the water of the cracking product, and at least a portion of the quench water.

A third aspect, which is the process of the second aspect, wherein the first cracking product temperature is from about 700° C. to about 1,300° C.; wherein the direct water quench comprises contacting at least a portion of the cracking product with quench water having a temperature of from about 30° C. to about 90° C.; and wherein the first cooled cracking product comprises the quench water in an amount of from about 1 wt. % to about 10 wt. %, based on the total weight of the first cooled cracking product.

A fourth aspect, which is the process of any one of the first through the third aspects, wherein the heat exchange medium comprises fuel gas and/or hydrocarbons; wherein the heated heat exchange medium comprises heated fuel gas and/or heated hydrocarbons, respectively; and wherein at least a portion of the heated fuel gas and/or at least a portion of the heated hydrocarbons are introduced to the ANJEVOC in step (a).

A fifth aspect, which is the process of any one of the first through the fourth aspects, wherein the heat exchange medium comprises water; wherein the heated heat exchange medium comprises steam; and wherein at least a portion of the steam is optionally introduced to the ANJEVOC in step (a).

A sixth aspect, which is the process of any one of the first through the fifth aspects further comprising recycling a first portion of the removed water as steam to the ANJEVOC in step (a).

A seventh aspect, which is the process of any one of the first through the sixth aspects, wherein oxygenates are present in the cracking product in an amount of from about 0.07 wt. % to about 1 wt. %, based on the total weight of the cracking product.

An eighth aspect, which is the process of any one of the first through the seventh aspects, wherein a second portion of the removed water is introduced to a waste water treatment unit to yield treated water; wherein the removed water is characterized by a first amount of oxygenates; wherein the treated water is characterized by a second amount of oxygenates; and wherein a weight ratio of the first amount of oxygenates to the second amount of oxygenates is equal to or greater than about 10.

A ninth aspect, which is the process of any one of the first through the eighth aspects, wherein $CO_2$ is present in the cracking product in an amount of from about 0.5 wt. % to about 10 wt. %, based on the total weight of the cracking product.

A tenth aspect, which is the process of any one of the first through the ninth aspects, wherein the $CO_2$-depleted cracked gas comprises $CO_2$ in an amount of less than about 10 ppmw, based on the total weight of the $CO_2$-depleted cracked gas.

An eleventh aspect, which is the process of any one of the first through the tenth aspects, wherein acetylene is present in the cracking product in an amount of from about 1 wt. % to about 25 wt. %, based on the total weight of the cracking product.

A twelfth aspect, which is the process of any one of the first through the eleventh aspects, wherein the $CO_2$-depleted cracked gas further comprises $C_{3+}$ hydrocarbons; and wherein at least a portion of acetylene in the $CO_2$-depleted cracked gas is converted to ethylene.

A thirteenth aspect, which is the process of the twelfth aspect, wherein the step (g) of separating at least a portion of the $CO_2$-depleted cracked gas comprises (1) separating at least a portion of the $CO_2$-depleted cracked gas into a $C_{2-}$ hydrocarbons stream and a $C_{3+}$ hydrocarbons stream; wherein the $C_{2-}$ hydrocarbons stream comprises ethylene, acetylene, ethane, methane, CO, and hydrogen; and wherein the $C_{3+}$ hydrocarbons stream comprises $C_{3+}$ hydrocarbons; (2) introducing at least a portion of the $C_{2-}$ hydrocarbons stream to an acetylene converter to yield an ethylene-enriched $C_{2-}$ hydrocarbons stream; wherein the ethylene-enriched $C_{2-}$ hydrocarbons stream comprises ethylene, ethane, methane, CO, and hydrogen; and wherein an amount of ethylene in the $C_{2-}$ hydrocarbons stream is lower than an amount of ethylene in the ethylene-enriched $C_{2-}$ hydrocarbons stream; and (3) separating at least a portion of the ethylene-enriched $C_{2-}$ hydrocarbons stream into ethylene, ethane, and tail gas.

A fourteenth aspect, which is the process of the twelfth aspect, wherein the step (g) of separating at least a portion of the $CO_2$-depleted cracked gas comprises (i) separating at least a portion of the $CO_2$-depleted cracked gas into the tail gas, a $C_2$ hydrocarbons stream, and a $C_{3+}$ hydrocarbons stream; wherein the $C_2$ hydrocarbons stream comprises ethylene, acetylene, and ethane; and wherein the $C_{3+}$ hydrocarbons stream comprises $C_{3+}$ hydrocarbons; (ii) introducing at least a portion of the $C_2$ hydrocarbons stream to an acetylene converter to yield an ethylene-enriched $C_2$ hydrocarbons stream; wherein the ethylene-enriched $C_2$ hydrocarbons stream comprises ethylene, and ethane; and wherein an amount of ethylene in the $C_2$ hydrocarbons stream is lower than an amount of ethylene in the ethylene-enriched $C_2$ hydrocarbons stream; and (iii) separating at least a portion of the ethylene-enriched $C_2$ hydrocarbons stream into ethylene, and ethane.

A fifteenth aspect, which is the process of any one of the first through the fourteenth aspects, wherein CO is present in the cracking product in an amount of from about 0.5 wt. % to about 10 wt. %, based on the total weight of the cracking product.

A sixteenth aspect, which is the process of any one of the first through the fifteenth aspects further comprising introducing at least a portion of the tail gas to a CO rejection unit to produce a CO-lean gas and a CO-rich gas; wherein the CO-lean gas comprises methane, CO, and hydrogen; and wherein an amount of CO in the CO-lean gas is lower than an amount of CO in the tail gas.

A seventeenth aspect, which is the process of the sixteenth aspect further comprising recycling at least a portion of the CO-lean gas as fuel gas to the ANJEVOC in step (a).

An eighteenth aspect, which is the process of any one of the sixteenth and the seventeenth aspects, wherein the CO-rich gas is further used as fuel.

A nineteenth aspect, which is process for producing ethylene comprising (a) introducing a fuel gas, hydrocarbons, an oxidant gas, and steam to an annular jet vortex chamber (ANJEVOC) to provide for a swirling fluid flow pattern within the ANJEVOC; wherein the ANJEVOC comprises a combustion zone and a cracking zone; wherein the combustion zone is upstream of the cracking zone; wherein the oxidant gas does not contact the fuel gas outside of the ANJEVOC; wherein the oxidant gas does not contact the hydrocarbons outside of the ANJEVOC; wherein the hydrocarbons comprise ethane and/or saturated hydrocarbons other than ethane; wherein at least a portion of the fuel gas and at least a portion of the oxidant gas contact each other in the combustion zone to produce a combustion product; wherein the combustion product comprises water and carbon dioxide; wherein the swirling fluid flow pattern provides for conveying at least a portion of the combustion product to the cracking zone; wherein the combustion product heats the hydrocarbons in the cracking zone to a temperature effective for a cracking reaction; and wherein at least a portion of the hydrocarbons undergoes a cracking reaction in the cracking zone to produce a cracking product; wherein the cracking product comprises ethylene, acetylene, ethane, methane, water, carbon dioxide ($CO_2$), carbon monoxide (CO), hydrogen, and oxygenates; wherein water is present in the cracking product in an amount of from about 10 wt. % to about 55 wt. %, based on the total weight of the cracking product; wherein oxygenates are present in the cracking product in an amount of from about 0.1 wt. % to about 1 wt. %, based on the total weight of the cracking product; wherein $CO_2$ is present in the cracking product in an amount of from about 1 wt. % to about 10 wt. %, based on the total weight of the cracking product; wherein CO is present in the cracking product in an amount of from about 1 wt. % to about 5 wt. %, based on the total weight of the cracking product;

wherein acetylene is present in the cracking product in an amount of from about 5 wt. % to about 20 wt. %, based on the total weight of the cracking product; and wherein the cracking product is characterized by a first cracking product temperature of from about 850° C. to about 1,100° C.; (b) contacting quench water having a temperature of from about 10° C. to about 40° C. with at least a portion of the cracking product in a first cracking product cooling zone with to yield a first cooled cracking product; wherein the first cooled cracking product comprises ethylene, acetylene, ethane, methane, $CO_2$, CO, hydrogen, oxygenates, at least a portion of the water of the cracking product, and at least a portion of the quench water; wherein the first cooled cracking product is characterized by a second cracking product temperature; wherein the second cracking product temperature is lower than the first cracking product temperature; wherein the difference between the first cracking product temperature and the second cracking product temperature is equal to or greater than about 40° C.; and wherein the first cracking product cooling zone is characterized by a residence time of less than about 500 milliseconds; (c) cooling at least a portion of the first cooled cracking product in a cracking product heat exchanger to yield a second cooled cracking product; wherein the second cooled cracking product is characterized by a third cracking product temperature; wherein the third cracking product temperature is lower than the second cracking product temperature; wherein the difference between the second cracking product temperature and the third cracking product temperature is equal to or greater than about 450° C.; and wherein cooling at least a portion of the first cooled cracking product comprises cooling at least a portion of the first cooled cracking product while heating a heat exchange medium in the cracking product heat exchanger to yield the second cooled cracking product and a heated heat exchange medium, respectively; (d) separating at least a portion of the second cooled cracking product into a cracked gas and removed water; wherein the removed water comprises at least a portion of the water of the cracking product; wherein the removed water comprises at least a portion of the oxygenates of the cracking product; wherein the removed water is characterized by a first amount of oxygenates; and wherein the cracked gas comprises ethylene, acetylene, ethane, methane, $CO_2$, CO, and hydrogen; (e) recycling a first portion of the removed water to the ANJEVOC in step (a); (f) introducing a second portion of the removed water to a waste water treatment unit to yield treated water; wherein the treated water is characterized by a second amount of oxygenates; and wherein a weight ratio of the first amount of oxygenates to the second amount of oxygenates is equal to or greater than about 10; (g) introducing at least a portion of the cracked gas to a continuous regeneration $CO_2$ removal unit to produce a $CO_2$-lean cracked gas; wherein the cracked gas is characterized by a first amount of $CO_2$; wherein the $CO_2$-lean cracked gas is characterized by a second amount of $CO_2$; and wherein a weight ratio of the first amount of $CO_2$ to the second amount of $CO_2$ is equal to or greater than about 10; (h) introducing at least a portion of the $CO_2$-lean cracked gas to a once-through $CO_2$ removal unit to produce a $CO_2$-depleted cracked gas; wherein the $CO_2$-depleted cracked gas comprises ethylene, acetylene, ethane, methane, CO, and hydrogen; and wherein the $CO_2$-depleted cracked gas comprises $CO_2$ in an amount of less than about 50 ppmw, based on the total weight of the $CO_2$-depleted cracked gas; (i) separating at least a portion of the $CO_2$-depleted cracked gas into ethylene, ethane, and a tail gas; wherein the tail gas comprises methane, CO, and hydrogen; (j) introducing at least a portion of the tail gas to a CO rejection unit to produce a CO-lean gas and a CO-rich gas; wherein the CO-lean gas comprises methane, CO, and hydrogen; and wherein an amount of CO in the CO-lean gas is lower than an amount of CO in the tail gas; and (k) recycling at least a portion of the CO-lean gas as fuel gas to the ANJEVOC in step (a).

A twentieth aspect, which is the process of the nineteenth aspect further comprising selectively converting at least a portion of the acetylene of the $CO_2$-depleted cracked gas to ethylene.

For the purpose of any U.S. national stage filing from this application, all publications and patents mentioned in this disclosure are incorporated herein by reference in their entireties, for the purpose of describing and disclosing the constructs and methodologies described in those publications, which might be used in connection with the methods of this disclosure. Any publications and patents discussed herein are provided solely for their disclosure prior to the filing date of the present application. Nothing herein is to be construed as an admission that the inventors are not entitled to antedate such disclosure by virtue of prior disclosure.

In any application before the United States Patent and Trademark Office, the Abstract of this application is provided for the purpose of satisfying the requirements of 37 C.F.R. § 1.72 and the purpose stated in 37 C.F.R. § 1.72(b) "to enable the United States Patent and Trademark Office and the public generally to determine quickly from a cursory inspection the nature and gist of the technical disclosure." Therefore, the Abstract of this application is not intended to be used to construe the scope of the claims or to limit the scope of the subject matter that is disclosed herein. Moreover, any headings that can be employed herein are also not intended to be used to construe the scope of the claims or to limit the scope of the subject matter that is disclosed herein. Any use of the past tense to describe an example otherwise indicated as constructive or prophetic is not intended to reflect that the constructive or prophetic example has actually been carried out.

While embodiments of the disclosure have been shown and described, modifications thereof can be made without departing from the spirit and teachings of the disclosure. The embodiments and examples described herein are exemplary only, and are not intended to be limiting. Many variations and modifications of the disclosure disclosed herein are possible and are within the scope of the disclosure.

Accordingly, the scope of protection is not limited by the description set out above but is only limited by the claims which follow, that scope including all equivalents of the subject matter of the claims. Each and every claim is incorporated into the specification as an embodiment of the present disclosure. Thus, the claims are a further description and are an addition to the detailed description of the present disclosure. The disclosures of all patents, patent applications, and publications cited herein are hereby incorporated by reference.

What is claimed is:

1. A process for producing ethylene comprising:
    (a) introducing a fuel gas, hydrocarbons, an oxidant gas, and steam to an annular jet vortex chamber (ANJEVOC) to provide for a swirling fluid flow pattern within the ANJEVOC; wherein the ANJEVOC comprises a combustion zone and a cracking zone; wherein the combustion zone is upstream of the cracking zone; wherein the oxidant gas does not contact the fuel gas outside of the ANJEVOC; wherein the oxidant gas does not contact the hydrocarbons outside of the ANJEVOC;

wherein the hydrocarbons comprise ethane and/or saturated hydrocarbons other than ethane; wherein at least a portion of the fuel gas and at least a portion of the oxidant gas contact each other in the combustion zone to produce a combustion product; wherein the combustion product comprises water and carbon dioxide; wherein the swirling fluid flow pattern provides for conveying at least a portion of the combustion product to the cracking zone; wherein the combustion product heats the hydrocarbons in the cracking zone to a temperature effective for a cracking reaction; and wherein at least a portion of the hydrocarbons undergoes a cracking reaction in the cracking zone to produce a cracking product; wherein the cracking product comprises ethylene, acetylene, ethane, methane, water, carbon dioxide ($CO_2$), carbon monoxide (CO), hydrogen, and oxygenates; wherein water is present in the cracking product in an amount of from about 10 wt. % to about 60 wt. %, based on the total weight of the cracking product; and wherein the cracking product is characterized by a first cracking product temperature;

(b) cooling at least a portion of the cracking product in a first cracking product cooling zone to yield a first cooled cracking product; wherein the first cooled cracking product is characterized by a second cracking product temperature; wherein the second cracking product temperature is lower than the first cracking product temperature; wherein the difference between the first cracking product temperature and the second cracking product temperature is equal to or greater than about 30° C.; and wherein the first cracking product cooling zone is characterized by a residence time of less than about 2,000 milliseconds;

(c) cooling at least a portion of the first cooled cracking product in a cracking product heat exchanger to yield a second cooled cracking product; wherein the second cooled cracking product is characterized by a third cracking product temperature; wherein the third cracking product temperature is lower than the second cracking product temperature; wherein the difference between the second cracking product temperature and the third cracking product temperature is equal to or greater than about 300° C.; and wherein cooling at least a portion of the first cooled cracking product comprises cooling at least a portion of the first cooled cracking product while heating a heat exchange medium in the cracking product heat exchanger to yield the second cooled cracking product and a heated heat exchange medium, respectively;

(d) separating at least a portion of the second cooled cracking product into a cracked gas and removed water; wherein the removed water comprises at least a portion of the water of the cracking product;

wherein the removed water comprises at least a portion of the oxygenates of the cracking product; and wherein the cracked gas comprises ethylene, acetylene, ethane, methane, $CO_2$, CO, and hydrogen;

(e) introducing at least a portion of the cracked gas to a continuous regeneration $CO_2$ removal unit to produce a $CO_2$-lean cracked gas; wherein the cracked gas is characterized by a first amount of $CO_2$;

wherein the $CO_2$-lean cracked gas is characterized by a second amount of $CO_2$; and wherein a weight ratio of the first amount of $CO_2$ to the second amount of $CO_2$ is equal to or greater than about 5;

(f) introducing at least a portion of the $CO_2$-lean cracked gas to a once-through $CO_2$ removal unit to produce a $CO_2$-depleted cracked gas; wherein the $CO_2$-depleted cracked gas comprises ethylene, acetylene, ethane, methane, CO, and hydrogen; and (g) separating at least a portion of the $CO_2$-depleted cracked gas into ethylene, ethane, and a tail gas; wherein the tail gas comprises methane, CO, and hydrogen.

2. The process of claim 1, wherein the step (b) of cooling at least a portion of the cracking product in a first cracking product cooling zone comprises direct water quench; wherein the direct water quench comprises contacting at least a portion of the cracking product with quench water to yield the first cooled cracking product; wherein the first cooled cracking product comprises ethylene, acetylene, ethane, methane, $CO_2$, CO, hydrogen, oxygenates, at least a portion of the water of the cracking product, and at least a portion of the quench water.

3. The process of claim 2, wherein the first cracking product temperature is from about 700° C. to about 1,300° C.; wherein the direct water quench comprises contacting at least a portion of the cracking product with quench water having a temperature of from about 30° C. to about 90° C.; and wherein the first cooled cracking product comprises the quench water in an amount of from about 1 wt. % to about 10 wt. %, based on the total weight of the first cooled cracking product.

4. The process of claim 1, wherein the heat exchange medium comprises fuel gas and/or hydrocarbons; wherein the heated heat exchange medium comprises heated fuel gas and/or heated hydrocarbons, respectively; and wherein at least a portion of the heated fuel gas and/or at least a portion of the heated hydrocarbons are introduced to the ANJEVOC in step (a).

5. The process of claim 1, wherein the heat exchange medium comprises water; wherein the heated heat exchange medium comprises steam; and wherein at least a portion of the steam is optionally introduced to the ANJEVOC in step (a).

6. The process of claim 1, further comprising recycling a first portion of the removed water as steam to the ANJEVOC in step (a).

7. The process of claim 1, wherein (1) oxygenates are present in the cracking product in an amount of from about 0.07 wt. % to about 1 wt. %, based on the total weight of the cracking product; (2) $CO_2$ is present in the cracking product in an amount of from about 0.5 wt. % to about 10 wt. %, based on the total weight of the cracking product; (3) CO is present in the cracking product in an amount of from about 0.5 wt. % to about 10 wt. %, based on the total weight of the cracking product; or (4) any combination of (1)-(3).

8. The process of claim 1, wherein a second portion of the removed water is introduced to a waste water treatment unit to yield treated water; wherein the removed water is characterized by a first amount of oxygenates; wherein the treated water is characterized by a second amount of oxygenates; and wherein a weight ratio of the first amount of oxygenates to the second amount of oxygenates is equal to or greater than about 10.

9. The process of claim 1, wherein the $CO_2$-depleted cracked gas comprises $CO_2$ in an amount of less than about 10 ppmw, based on the total weight of the $CO_2$-depleted cracked gas.

10. The process of claim 1, wherein acetylene is present in the cracking product in an amount of from about 1 wt. % to about 25 wt. %, based on the total weight of the cracking product.

11. The process of claim 1, wherein the $CO_2$-depleted cracked gas further comprises $C_{3+}$ hydrocarbons; and wherein at least a portion of acetylene in the $CO_2$-depleted cracked gas is converted to ethylene.

12. The process of claim 11, wherein the step (g) of separating at least a portion of the $CO_2$-depleted cracked gas comprises (1) separating at least a portion of the $CO_2$-depleted cracked gas into a $C_{2-}$ hydrocarbons stream and a $C_{3+}$ hydrocarbons stream; wherein the $C_{2-}$ hydrocarbons stream comprises ethylene, acetylene, ethane, methane, CO, and hydrogen; and wherein the $C_{3+}$ hydrocarbons stream comprises $C_{3+}$ hydrocarbons; (2) introducing at least a portion of the $C_{2-}$ hydrocarbons stream to an acetylene converter to yield an ethylene-enriched $C_{2-}$ hydrocarbons stream; wherein the ethylene-enriched $C_{2-}$ hydrocarbons stream comprises ethylene, ethane, methane, CO, and hydrogen; and wherein an amount of ethylene in the $C_{2-}$ hydrocarbons stream is lower than an amount of ethylene in the ethylene-enriched $C_{2-}$ hydrocarbons stream; and (3) separating at least a portion of the ethylene-enriched $C_{2-}$ hydrocarbons stream into ethylene, ethane, and tail gas.

13. The process of claim 11, wherein the step (g) of separating at least a portion of the $CO_2$-depleted cracked gas comprises (i) separating at least a portion of the $CO_2$-depleted cracked gas into the tail gas, a $C_2$ hydrocarbons stream, and a $C_{3+}$ hydrocarbons stream; wherein the $C_2$ hydrocarbons stream comprises ethylene, acetylene, and ethane; and wherein the $C_{3+}$ hydrocarbons stream comprises $C_{3+}$ hydrocarbons; (ii) introducing at least a portion of the $C_2$ hydrocarbons stream to an acetylene converter to yield an ethylene-enriched $C_2$ hydrocarbons stream; wherein the ethylene-enriched $C_2$ hydrocarbons stream comprises ethylene, and ethane; and wherein an amount of ethylene in the $C_2$ hydrocarbons stream is lower than an amount of ethylene in the ethylene-enriched $C_2$ hydrocarbons stream; and (iii) separating at least a portion of the ethylene-enriched $C_2$ hydrocarbons stream into ethylene, and ethane.

14. The process of claim 1, further comprising introducing at least a portion of the tail gas to a CO rejection unit to produce a CO-lean gas and a CO-rich gas; wherein the CO-lean gas comprises methane, CO, and hydrogen; and wherein an amount of CO in the CO-lean gas is lower than an amount of CO in the tail gas.

15. The process of claim 14 further comprising recycling at least a portion of the CO-lean gas as fuel gas to the ANJEVOC in step (a).

16. The process of claim 1, further comprising:
introducing at least a portion of acetylene in the CO2-depleted cracked gas into an acetylene converter to yield an ethylene-enriched C2 hydrocarbons stream; and
recycling at least a portion of the ethylene-enriched C2 hydrocarbons stream to the acetylene converter.

* * * * *